United States Patent
Cabiri

(10) Patent No.: US 8,241,351 B2
(45) Date of Patent: Aug. 14, 2012

(54) ADJUSTABLE PARTIAL ANNULOPLASTY RING AND MECHANISM THEREFOR

(75) Inventor: Oz Cabiri, Macabim-Reut (IL)

(73) Assignee: Valtech Cardio, Ltd., Or Yehuda (IL)

( * ) Notice: Subject to any disclaimer, the term of this patent is extended or adjusted under 35 U.S.C. 154(b) by 108 days.

(21) Appl. No.: 12/341,960

(22) Filed: Dec. 22, 2008

(65) Prior Publication Data
US 2010/0161047 A1 Jun. 24, 2010

(51) Int. Cl.
*A61F 2/24* (2006.01)
(52) U.S. Cl. ........................ 623/2.37; 623/2.36
(58) Field of Classification Search .......... 623/2.37
See application file for complete search history.

(56) References Cited

U.S. PATENT DOCUMENTS

| | | | |
|---|---|---|---|
| 4,602,911 A | 7/1986 | Ahmadi et al. | |
| 4,625,727 A | 12/1986 | Leiboff | |
| 4,778,468 A | 10/1988 | Hunt et al. | |
| 4,917,698 A | 4/1990 | Carpentier et al. | |
| 5,061,277 A | 10/1991 | Carpentier et al. | |
| 5,104,407 A | 4/1992 | Lam et al. | |
| 5,108,420 A | 4/1992 | Marks | |
| 5,306,296 A | 4/1994 | Wright et al. | |
| 5,450,860 A | 9/1995 | O'Connor | |
| 5,477,856 A | 12/1995 | Lundquist | |
| 5,669,919 A | 9/1997 | Sanders et al. | |
| 5,674,279 A | 10/1997 | Wright et al. | |
| 5,843,120 A | 12/1998 | Israel et al. | |
| 5,876,373 A | 3/1999 | Giba et al. | |
| 5,961,440 A | 10/1999 | Schweich et al. | |
| 5,961,539 A | 10/1999 | Northrup, III et al. | |
| 6,045,497 A | 4/2000 | Schweich et al. | |
| 6,050,936 A | 4/2000 | Schweich et al. | |
| 6,059,715 A | 5/2000 | Schweich et al. | |
| 6,165,119 A | 12/2000 | Schweich et al. | |
| 6,231,602 B1 * | 5/2001 | Carpentier et al. | 623/2.36 |

(Continued)

FOREIGN PATENT DOCUMENTS

WO 92/05093 4/1992

(Continued)

OTHER PUBLICATIONS

O'Reilly S et al., "Heart valve surgery pushes the envelope," Medtech Insight 8(3): 73, 99-108 (2006).

(Continued)

*Primary Examiner* — Thomas J Sweet
*Assistant Examiner* — Jacqueline Woznicki
(74) *Attorney, Agent, or Firm* — Kilpatrick Townsend & Stockton LLP

(57) ABSTRACT

Apparatus is provided that is configured to be implanted in a body of a subject, comprising an implant structure having first and second portions thereof, a spool coupled to the implant structure in a vicinity of the first portion thereof, and a flexible member coupled at a first end thereof to the spool, and not attached at a second end thereof to the spool. The flexible member, in response to rotation of the spool in a first direction thereof, is configured to be wound around the spool, and, responsively, to pull the second end of the flexible member toward the first end of the implant structure, and responsively to draw the first and second portions of the implant structure toward each other. Other embodiments are also described.

34 Claims, 13 Drawing Sheets

U.S. PATENT DOCUMENTS

| | | | |
|---|---|---|---|
| 6,251,092 B1 | 6/2001 | Qin et al. |
| 6,319,281 B1 | 11/2001 | Patel |
| 6,332,893 B1 | 12/2001 | Mortier et al. |
| 6,406,420 B1 | 6/2002 | McCarthy et al. |
| 6,451,054 B1 | 9/2002 | Stevens |
| 6,524,338 B1 | 2/2003 | Gundry |
| 6,537,314 B2 | 3/2003 | Langberg et al. |
| 6,564,805 B2 | 5/2003 | Garrison et al. |
| 6,569,198 B1 | 5/2003 | Wilson et al. |
| 6,589,160 B2 | 7/2003 | Schweich et al. |
| 6,602,288 B1 | 8/2003 | Cosgrove |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,682,558 B2 | 1/2004 | Tu et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,718,985 B2 | 4/2004 | Hlavka et al. |
| 6,723,038 B1 | 4/2004 | Schroeder et al. |
| 6,726,716 B2 * | 4/2004 | Marquez ............... 623/2.36 |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,510 B2 | 7/2004 | Vidlund et al. |
| 6,786,924 B2 | 9/2004 | Ryan et al. |
| 6,802,319 B2 | 10/2004 | Stevens et al. |
| 6,805,710 B2 | 10/2004 | Bolling et al. |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,482 B2 | 6/2005 | McCarthy et al. |
| 6,986,775 B2 | 1/2006 | Morales et al. |
| 6,989,028 B2 | 1/2006 | Lashinski et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,159,593 B2 | 1/2007 | McCarthy |
| 7,169,187 B2 | 1/2007 | Datta et al. |
| 7,175,660 B2 | 2/2007 | Cartledge et al. |
| 7,186,262 B2 | 3/2007 | Saadat |
| 7,189,199 B2 | 3/2007 | McCarthy et al. |
| 7,226,467 B2 | 6/2007 | Lucatero et al. |
| 7,238,191 B2 * | 7/2007 | Bachmann ............... 606/151 |
| 7,294,148 B2 | 11/2007 | McCarthy |
| 7,297,150 B2 | 11/2007 | Cartledge et al. |
| 7,311,728 B2 | 12/2007 | Solem et al. |
| 7,316,710 B1 | 1/2008 | Cheng et al. |
| 7,329,280 B2 | 2/2008 | Bolling et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,452,376 B2 | 11/2008 | Lim et al. |
| 7,455,690 B2 | 11/2008 | Cartledge et al. |
| 7,507,252 B2 | 3/2009 | Lashinski et al. |
| 7,530,995 B2 | 5/2009 | Quijano |
| 7,549,983 B2 | 6/2009 | Roue et al. |
| 7,563,267 B2 | 7/2009 | Goldfarb et al. |
| 7,563,273 B2 | 7/2009 | Goldfarb et al. |
| 7,588,582 B2 | 9/2009 | Starksen et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,993,368 B2 | 8/2011 | Gambale et al. |
| 2002/0087048 A1 | 7/2002 | Brock et al. |
| 2002/0103532 A1 | 8/2002 | Langberg et al. |
| 2002/0173841 A1 | 11/2002 | Ortiz et al. |
| 2002/0177904 A1 | 11/2002 | Huxel et al. |
| 2003/0050693 A1 | 3/2003 | Quijano et al. |
| 2003/0105519 A1 | 6/2003 | Fasol et al. |
| 2003/0167062 A1 | 9/2003 | Gambale et al. |
| 2003/0233142 A1 * | 12/2003 | Morales et al. ............... 623/2.37 |
| 2004/0024451 A1 | 2/2004 | Johnson et al. |
| 2004/0049207 A1 | 3/2004 | Goldfarb et al. |
| 2004/0092962 A1 | 5/2004 | Thornton et al. |
| 2004/0122514 A1 | 6/2004 | Forgarty et al. |
| 2004/0148021 A1 | 7/2004 | Cartledge et al. |
| 2004/0181287 A1 | 9/2004 | Gellman |
| 2004/0236419 A1 | 11/2004 | Milo |
| 2005/0004668 A1 | 1/2005 | Aklog et al. |
| 2005/0016560 A1 | 1/2005 | Voughlohn |
| 2005/0055087 A1 | 3/2005 | Starksen |
| 2005/0060030 A1 | 3/2005 | Lashinski et al. |
| 2005/0090827 A1 | 4/2005 | Gedebou |
| 2005/0171601 A1 | 8/2005 | Cosgrove et al. |
| 2005/0177228 A1 | 8/2005 | Solem et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0288781 A1 | 12/2005 | Moaddeb et al. |
| 2006/0020326 A9 | 1/2006 | Bolduc et al. |
| 2006/0025787 A1 | 2/2006 | Morales et al. |
| 2006/0041319 A1 | 2/2006 | Taylor et al. |
| 2006/0069429 A1 | 3/2006 | Spence et al. |
| 2006/0129166 A1 | 6/2006 | Lavelle |
| 2006/0161265 A1 | 7/2006 | Levine et al. |
| 2006/0241656 A1 | 10/2006 | Starksen et al. |
| 2006/0241748 A1 | 10/2006 | Lee et al. |
| 2006/0282161 A1 | 12/2006 | Huyn et al. |
| 2006/0287716 A1 | 12/2006 | Banbury et al. |
| 2007/0016287 A1 * | 1/2007 | Cartledge et al. ............ 623/2.11 |
| 2007/0027536 A1 | 2/2007 | Mihaljevic et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0080188 A1 | 4/2007 | Spence et al. |
| 2007/0112422 A1 | 5/2007 | Dehdashtian |
| 2007/0118151 A1 | 5/2007 | Davidson |
| 2007/0162111 A1 | 7/2007 | Fukamachi et al. |
| 2007/0198082 A1 | 8/2007 | Kapadia et al. |
| 2007/0213582 A1 | 9/2007 | Zollinger et al. |
| 2007/0219558 A1 | 9/2007 | Deutsch |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0282375 A1 | 12/2007 | Hindrichs et al. |
| 2008/0004697 A1 | 1/2008 | Lichtenstein et al. |
| 2008/0035160 A1 | 2/2008 | Wodson et al. |
| 2008/0058595 A1 | 3/2008 | Snoke et al. |
| 2008/0086203 A1 | 4/2008 | Roberts |
| 2008/0097523 A1 | 4/2008 | Bolduc et al. |
| 2008/0195126 A1 | 8/2008 | Solem |
| 2008/0262609 A1 | 10/2008 | Gross et al. |
| 2008/0288044 A1 | 11/2008 | Osborne |
| 2009/0043153 A1 | 2/2009 | Zollinger et al. |
| 2009/0171439 A1 | 7/2009 | Nissl |
| 2009/0177266 A1 | 7/2009 | Powell et al. |
| 2009/0326648 A1 | 12/2009 | Machold et al. |
| 2010/0023118 A1 | 1/2010 | Medlock et al. |
| 2010/0042147 A1 | 2/2010 | Janovsky et al. |
| 2010/0130992 A1 | 5/2010 | Machold et al. |
| 2010/0161041 A1 | 6/2010 | Maisano et al. |
| 2010/0161043 A1 | 6/2010 | Maisano et al. |
| 2010/0174358 A1 | 7/2010 | Rabkin et al. |
| 2010/0179574 A1 | 7/2010 | Longoria |
| 2010/0234935 A1 | 9/2010 | Bashiri et al. |
| 2010/0324598 A1 | 12/2010 | Anderson |

| | | |
|---|---|---|
| 2011/0029066 A1 | 2/2011 | Gilad et al. |
| 2011/0093002 A1 | 4/2011 | Rucker et al. |
| 2011/0184510 A1 | 7/2011 | Maisano et al. |

FOREIGN PATENT DOCUMENTS

| | | |
|---|---|---|
| WO | WO 01/26586 | 4/2001 |
| WO | WO 02/085251 | 10/2002 |
| WO | WO 02/085252 | 10/2002 |
| WO | 2005/021063 | 3/2005 |
| WO | WO 2006/097931 | 3/2006 |
| WO | WO 2006/116558 | 11/2006 |
| WO | WO 2007/136783 | 11/2007 |
| WO | WO 2008/068756 | 6/2008 |
| WO | WO 2010/073246 | 7/2010 |
| WO | 2011/089601 | 7/2011 |

OTHER PUBLICATIONS

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Swain CP et al., "An endoscopically deliverable tissue-transfixing device for securing biosensors in the gastrointestinal tract," Gastrointestinal Endoscopy 40(6): 730-734 (1994).

Odell JA et al., "Early Results of a Simplified Method of Mitral Valve Annuloplasty," Circulation 92:150-154 (1995).

An International Search Report dated Sep. 8, 2009, which issued during the prosecution of Applicant's PCT/IL09/00593.

U.S. Appl. No. 60/873,075, filed Dec. 5, 2006.
U.S. Appl. No. 60/902,146, filed Feb. 16, 2007.
U.S. Appl. No. 61/001,013, filed Oct. 29, 2007.
U.S. Appl. No. 61/132,295, filed Jun. 16, 2008.

"Two dimensional real-time ultrasonic imaging of the heart and great vessels", Mayo Clin Proc. vol. 53:271-303, 1978.

An International Search Report dated Jun. 10, 2010, which issued during the prosecution of Applicant's PCT/IL09/01209.

An Office Action dated Apr. 6, 2010, which issued during the prosecution of Applicant's U.S. Appl. No. 12/484,512.

An International Search Report and a Written Opinion, both dated Aug. 17, 2010, which issued during the prosecution of Applicant's PCT/IL10/00357.

An Office Action dated Oct. 6, 2010, which issued during the prosecution of Applicant's U.S. Appl. No. 12/484,512.

An Office Action dated Mar. 9, 2012, which issued during the prosecution of U.S. Appl. No. 13/689,635.

An Office Action dated Sep. 28, 2011, which issued during the prosecution of U.S. Appl. No. 12/437,103.

An Office Action dated Dec. 29, 2011, which issued during the prosecution of U.S. Appl. No. 12/563,952.

An International Search Report dated Dec. 29, 2010, which issued during the prosecution of Applicant's PCT/IL2010/000358.

An International Search Report dated Jun. 10, 2010, which issued during the prosecution of Applicant's PCT/IL2009/001209.

An International Search Report dated Nov. 23, 2011, which issued during the prosecution of Applicant's PCT/IL2011/000446.

An International Search Report dated Nov. 11, 2011, which issued during the prosecution of Applicant's PCT/IL2011/000404.

An International Search Report dated Feb. 2, 2012, which issued during the prosecution of Applicant's PCT/IL2011/000600.

An International Preliminary Report on Patentability dated Nov. 29, 2011 which issued during the prosecution of Applicant's PCT/IL2010/000358.

An International Search Report dated May 19, 2011, which issued during the prosecution of Applicant's PCT/IL2011/00064.

An Office Action dated Jan. 23, 2012, which issued during the prosecution of U.S. Appl. No. 12/692,061.

* cited by examiner

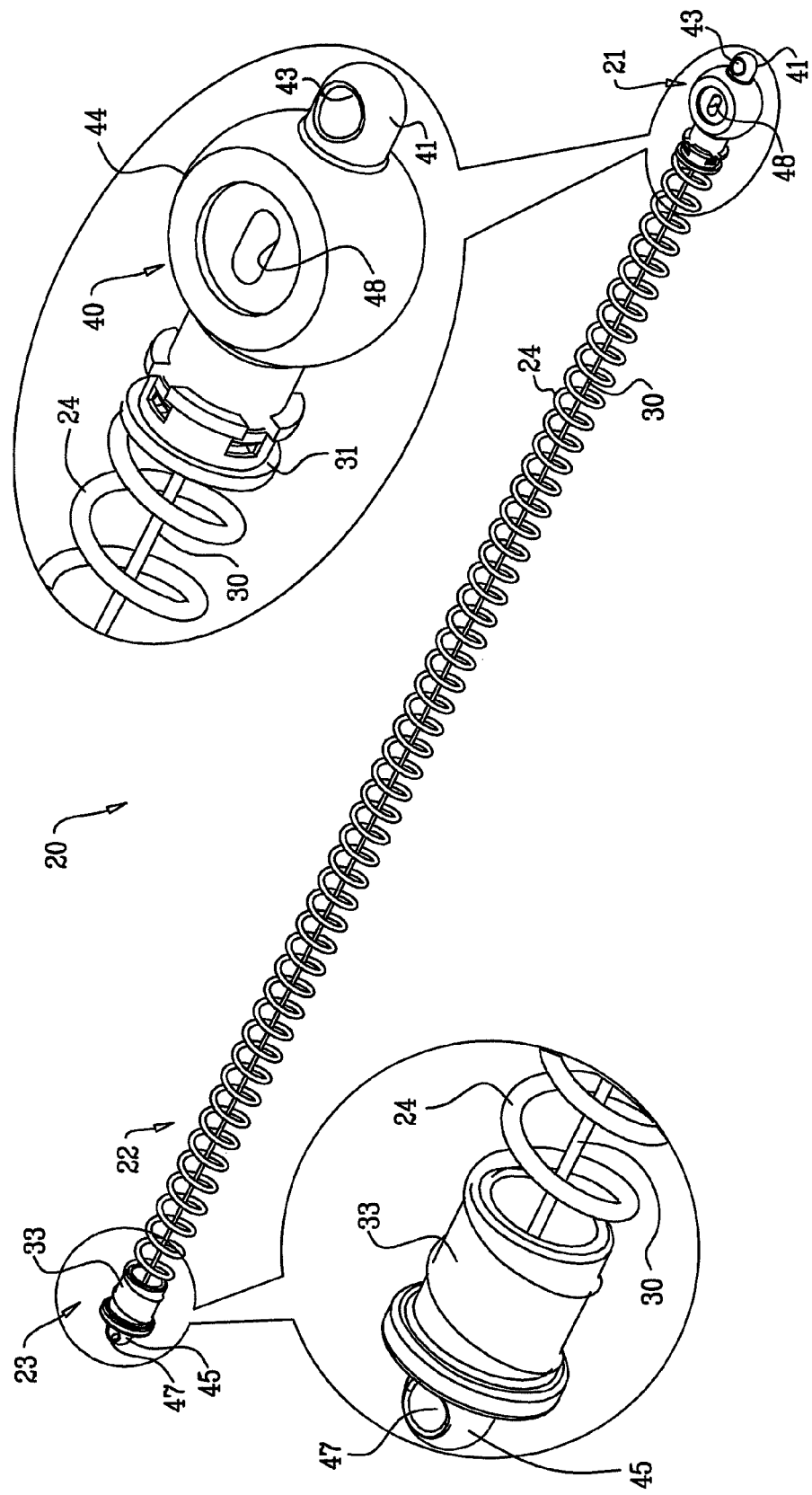

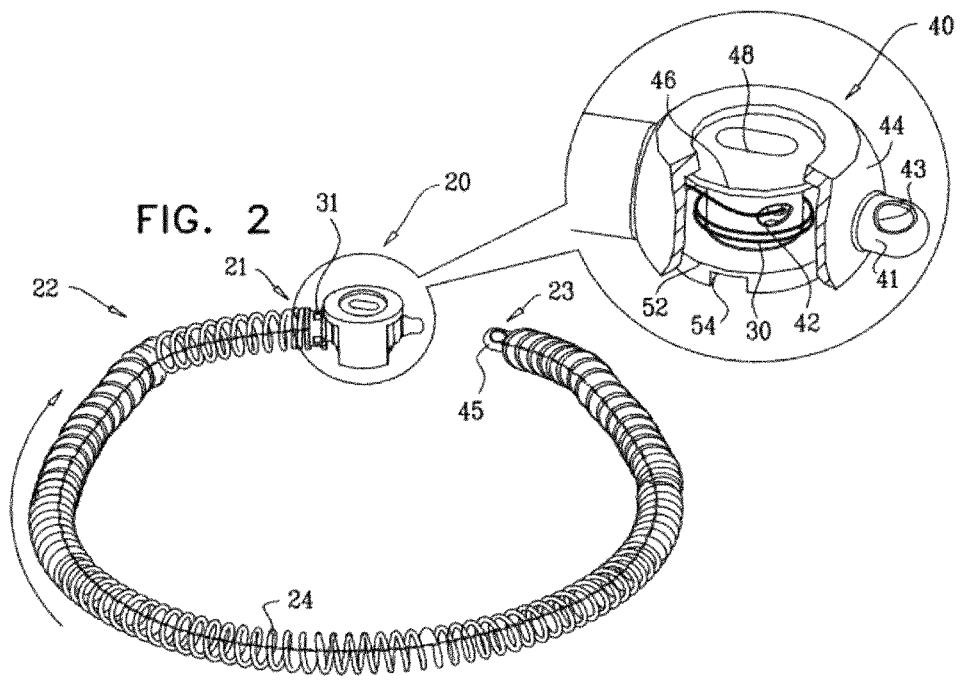
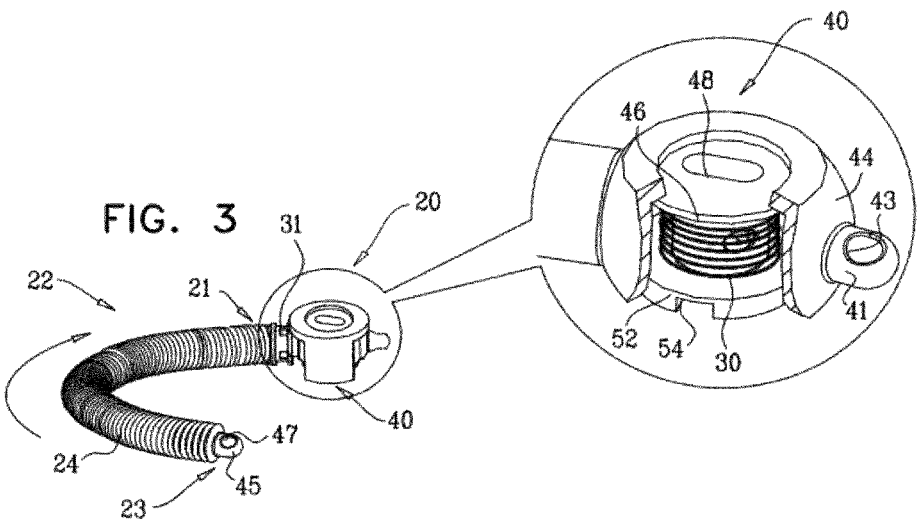

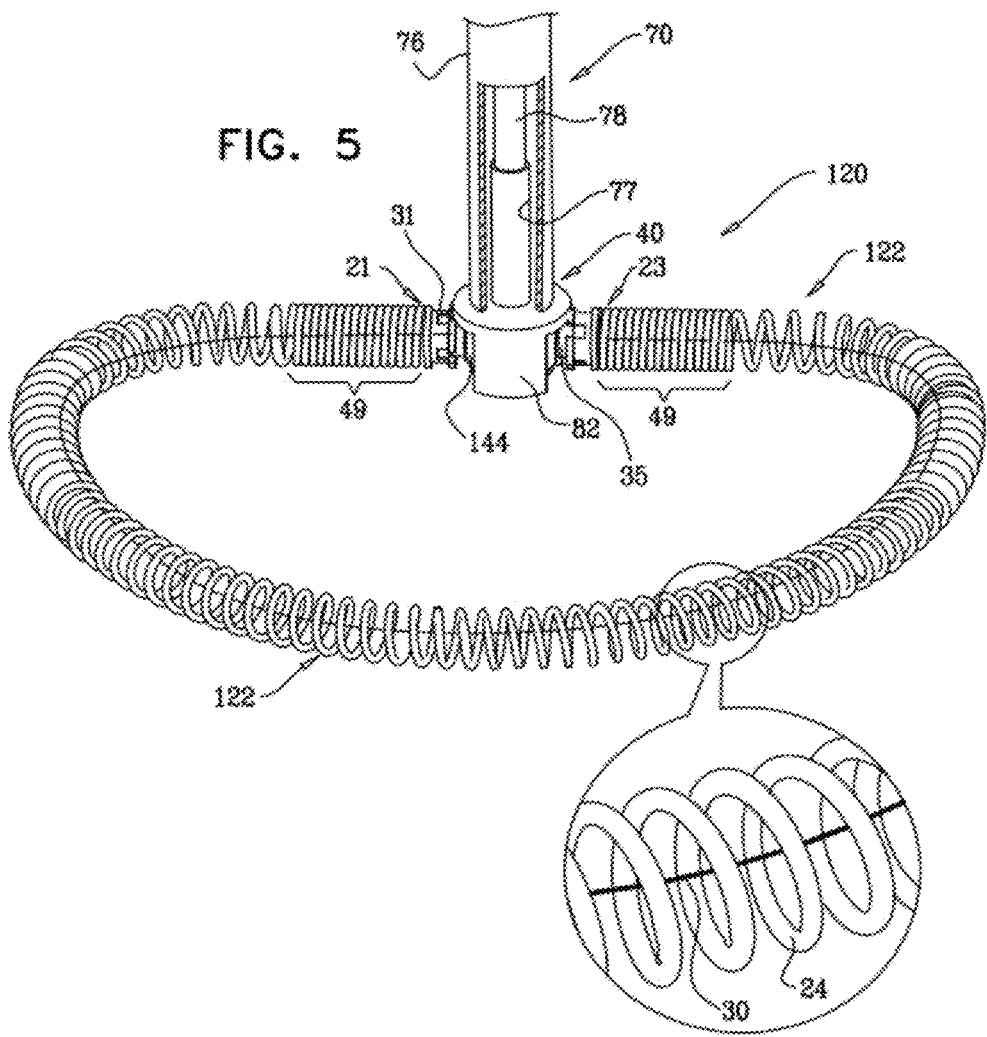

FIG. 6A
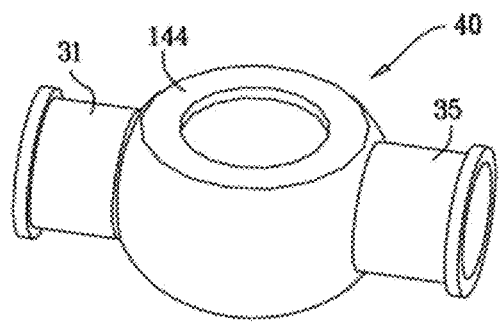
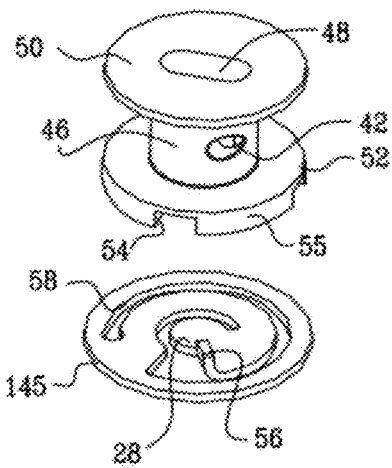
FIG. 6B
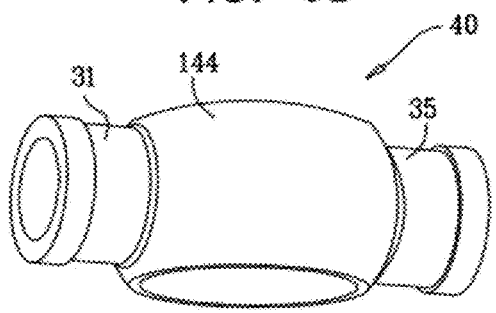
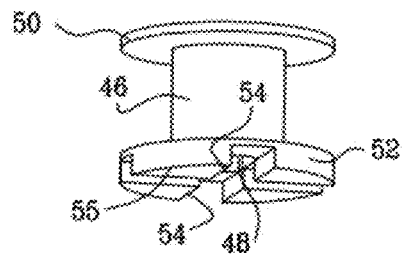

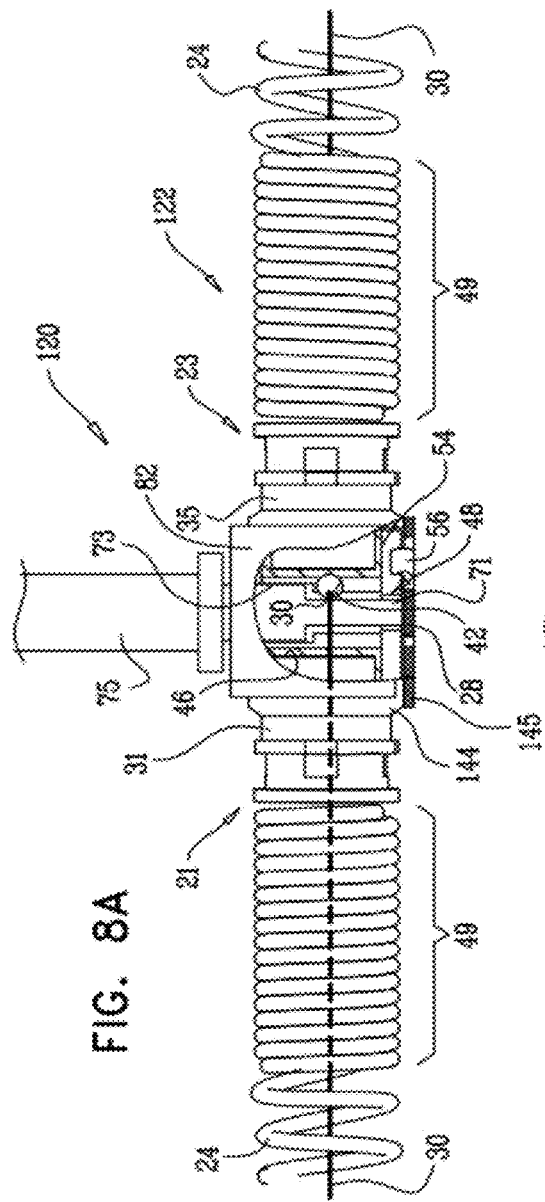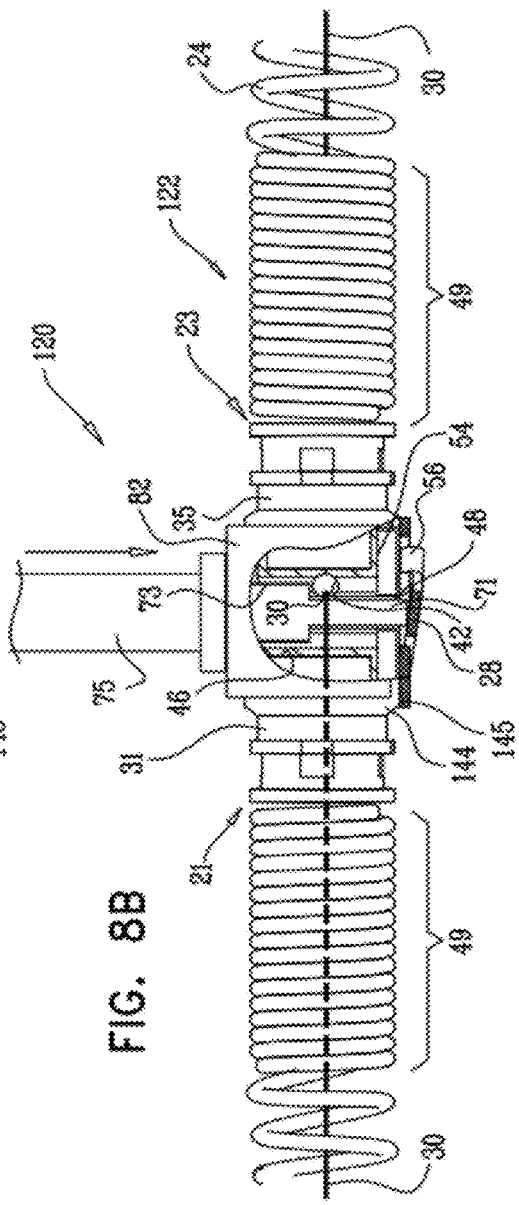

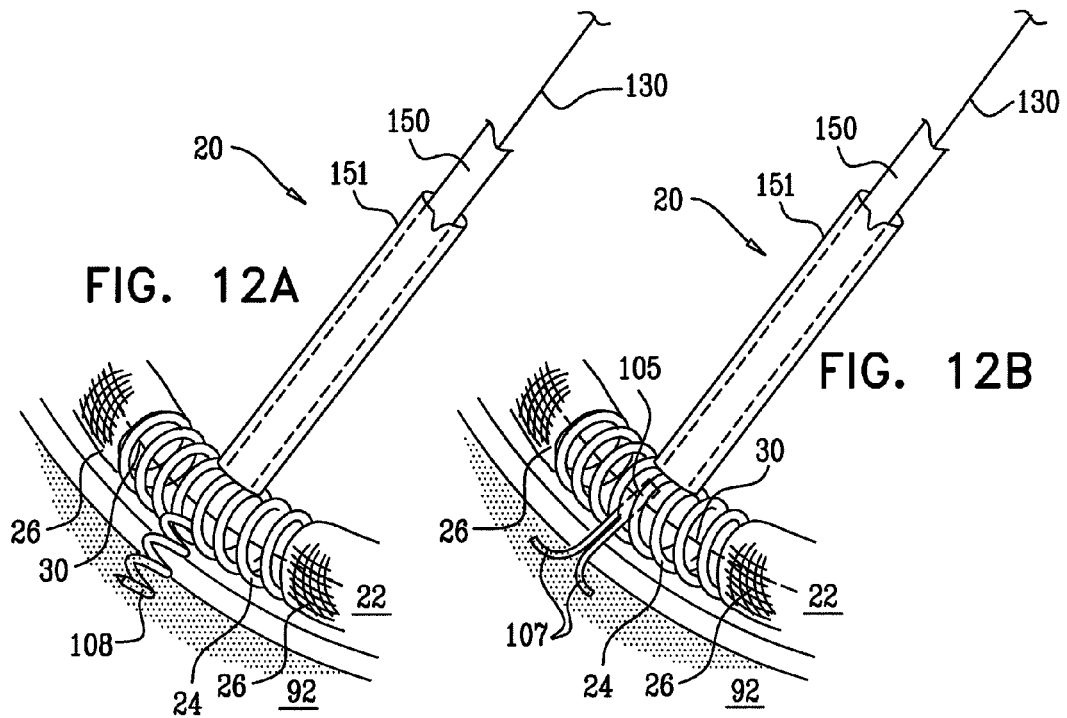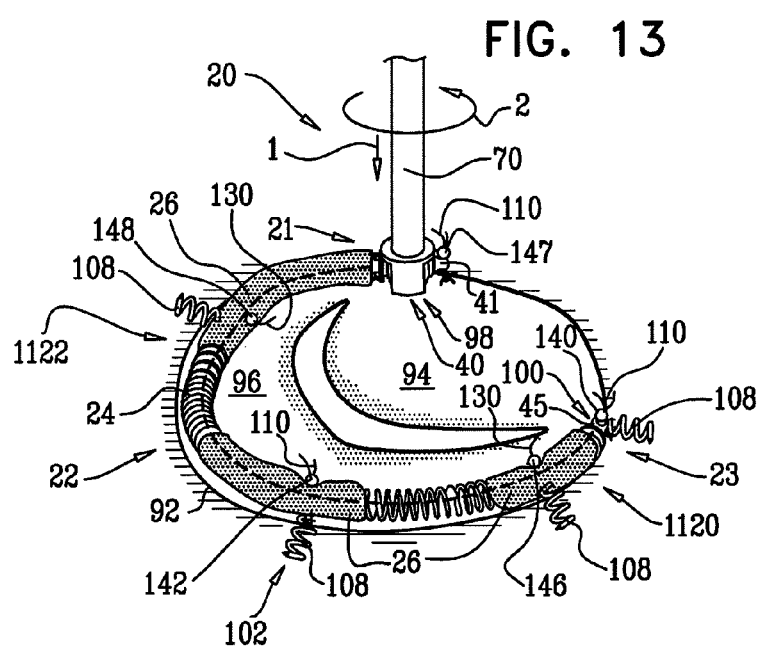

ADJUSTABLE PARTIAL ANNULOPLASTY RING AND MECHANISM THEREFOR

CROSS-REFERENCES TO RELATED APPLICATIONS

The present application is related to PCT Publication WO 06/097931 to Gross et al., entitled, "Mitral Valve treatment techniques," filed Mar. 15, 2006, which is incorporated herein by reference.

FIELD OF THE INVENTION

The present invention relates in general to valve repair. More specifically, the present invention relates to repair of a mitral valve of a patient.

BACKGROUND OF THE INVENTION

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium. U.S. Pat. No. 7,431,692 to Zollinger et al. describes an adjustable support pad for adjustably holding a tensioning line used to apply tension to a body organ. The adjustable support pad can include a locking mechanism for preventing slidable movement of the tensioning element in one or both directions. The locking mechanism may include spring-loaded locks, rotatable cam-like structures, and/or rotatable spool structures. The adjustable support pad may be formed from rigid, semi-rigid, and/or flexible materials, and may be formed to conform to the outer surface of a body organ. The adjustable support pad can be configured to adjustably hold one or more separate tensioning lines, and to provide for independent adjustment of one or more tensioning lines or groups thereof.

U.S. Patent Application Publication 2007/0016287 to Cartledge et al. describes an implantable device for controlling shape and/or size of an anatomical structure or lumen. The implantable device has an adjustable member configured to adjust the dimensions of the implantable device. The implantable device is housed in a catheter and insertable from a minimally invasive surgical entry. An adjustment tool actuates the adjustable member and provide for adjustment before, during or after the anatomical structure or lumen resumes near normal to normal physiologic function.

U.S. Patent Application Publication 2004/0236419 to Milo describes methods for reconfiguring an atrioventricular heart valve that may use systems comprising a partial or complete annuloplasty rings proportioned to reconfigure a heart valve that has become in some way incompetent, a pair of trigonal sutures or implantable anchors, and a plurality of staples which may have pairs of legs that are sized and shaped for association with the ring at spaced locations along its length. These systems permit relative axial movement between the staples and the ring, whereby a patient's heart valve can be reconfigured in a manner that does not deter subtle shifting of the native valve components. Shape-memory alloy material staples may have legs with free ends that interlock following implantation. Annuloplasty rings may be complete or partial and may be fenestrated. One alternative method routes a flexible wire, preferably of shape-memory material, through the bights of pre-implanted staples. Other alternative systems use linkers of shape-memory material having hooked ends to interengage with staples or other implanted supports which, following implantation, decrease in effective length and pull the staples or other supports toward one another so as to create desired curvature of the reconfigured valve. These linkers may be separate from the supports or may be integral with them and may have a variety of shapes and forms. Various ones of these systems are described as being implanted non-invasively using a delivery catheter.

U.S. Patent Application Publication 2005/0171601 to Cosgrove et al. describes an annuloplasty repair segment and template for heart valve annulus repair. The elongate flexible template may form a distal part of a holder that also has a proximal handle. Alternatively, the template may be releasably attached to a mandrel that slides within a delivery sheath, the template being released from the end of the sheath to enable manipulation by a surgeon. A tether connecting the template and mandrel may also be provided. The template may be elastic, temperature responsive, or multiple linked segments. The template may be aligned with the handle and form a two- or three-dimensional curve out of alignment with the handle such that the annuloplasty repair segment attached thereto conforms to the curve. The template may be actively or passively converted between its straight and curved positions. The combined holder and ring is especially suited for minimally-invasive surgeries in which the combination is delivered to an implantation site through a small access incision with or without a cannula, or through a catheter passed though the patient's vasculature.

The following patents and patent application publications, relevant portions of which are incorporated herein by reference, may be of interest:

PCT Patent Application Publication WO 07/136783 to Cartledge et al.
U.S. Pat. No. 5,306,296 to Wright et al.
U.S. Pat. No. 6,569,198 to Wilson et al.
U.S. Pat. No. 6,619,291 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
U.S. Patent Application Publication 2003/0050693 to Quijano et al
U.S. Patent Application Publication 2003/0167062 to Gambale et al.
U.S. Patent Application Publication 2004/0024451 to Johnson et al.
U.S. Patent Application Publication 2004/0148021 to Cartledge et al.
U.S. Patent Application Publication 2005/0288781 to Moaddeb et al.
U.S. Patent Application Publication 2007/0080188 to Spence et al.

The following articles, which are incorporated herein by reference, may be of interest:

O'Reilly S et al., "Heart valve surgery pushes the envelope," Medtech Insight 8(3): 73, 99-108 (2006)

Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003)

Swain C P et al., "An endoscopically deliverable tissue-transfixing device for securing biosensors in the gastrointestinal tract," Gastrointestinal Endoscopy 40(6): 730-734 (1994)

Odell J A et al., "Early Results of a Simplified Method of Mitral Valve Annuloplasty," Circulation 92:150-154 (1995)

BRIEF SUMMARY OF THE INVENTION

In some embodiments of the present invention, apparatus is provided comprising an adjustable annuloplasty structure configured to repair a dilated mitral valve of a patient. At least a portion of the annuloplasty structure comprises a flexible, longitudinally-compressible segment (e.g., coiled structures, stent-like struts, or a braided mesh). The annuloplasty structure is shaped to define a lumen thereof that houses a flexible member, e.g., a contracting wire. The annuloplasty structure comprises a contracting mechanism which facilitates contracting of the annuloplasty structure. The contracting mechanism comprises a spool to which a first end of the flexible member is coupled. Typically, a second end of the flexible member is not coupled to the spool, but rather is coupled to a portion of the annuloplasty structure.

In some embodiments, the annuloplasty structure is shaped to provide an adjustable partial annuloplasty structure. In such an embodiment, the annuloplasty structure comprises an elongate structure which is coupled at a first end thereof to the contracting mechanism. The first end of the flexible member is coupled to the spool while the second end of the flexible member is coupled to a second end of the elongate structure.

Typically, during a resting state thereof, the elongate structure assumes a linear configuration. The elongate structure is made to assume a curved configuration in which the elongate structure provides a partial annuloplasty ring. In some embodiments, the first and second ends of the elongate structure are coupled together such that the elongate structure forms an annuloplasty ring. For example, the first and second ends of the elongate element are each coupled to a housing surrounding the contracting mechanism. In either embodiment, the annuloplasty structure is contracted by the contracting mechanism such that the dimensions of the annuloplasty structure are reduced and the structure contracts radially, thereby contracting the annulus.

As the operating physician rotates the spool of the contracting mechanism, a portion of the flexible member is wound around the spool. In response to continued rotation of the spool, increasing portions of the flexible member are wrapped around the spool, which causes the flexible member to pull on the second end of the elongate structure toward the contracting mechanism. Responsively, the compressible element is compressed between the first and second ends of the elongate structure. Thus, the flexible member helps regulate a spatial configuration of the annuloplasty structure.

In some embodiments, during a resting state, the annuloplasty structure defines a linear shape. Subsequently, during implantation, the annuloplasty structure is made to assume at least part of a ring-shaped structure. The annuloplasty structure may be advanced toward the annulus of a valve in any suitable procedure, e.g., transcatheter, minimally invasive, or in an open heart procedure.

There is therefore provided, in accordance with an embodiment of the present invention, apparatus configured to be implanted in a body of a subject, including:

an implant structure having first and second portions thereof;
a spool coupled to the implant structure in a vicinity of the first portion thereof; and
a flexible member coupled at a first end thereof to the spool, and not attached at a second end thereof to the spool, the flexible member:
in response to rotation of the spool in a first direction thereof, configured to be wound around the spool, and, responsively, to pull the second end of the flexible member toward the first end of the implant structure, and responsively to draw the first and second portions of the implant structure toward each other.

In an embodiment, the flexible member is configured to be unwound from around the spool and to facilitate expansion of the implant structure in response to rotation of the spool in a second direction thereof that is opposite the first direction.

In an embodiment, the implant structure includes expanded polytetrafluoroethylene (ePTFE).

In an embodiment, the implant structure is coated with polytetrafluoroethylene.

In an embodiment:
the implant structure is configured to be implanted along an annulus of a mitral valve of the subject,
the flexible member is configured to contract the implant structure in response to the rotation of the spool in the first direction, and
the implant structure is configured to contract the annulus in response to the contraction thereof.

In an embodiment, the second portion of the implant structure is coupled to the spool in a manner that causes the implant structure to be shaped to define an annuloplasty ring.

In an embodiment, the apparatus is configured to be implanted along an annulus of a mitral valve of the subject, and the apparatus is configured to be transcatheterally advanced toward the annulus.

In an embodiment, the apparatus includes a locking mechanism coupled to the implant structure and configured to restrict rotation of the spool.

In an embodiment:
the first and second portions are disposed adjacently to first and second ends of the implant structure, respectively,
the apparatus is configured to be implanted along an annulus of a mitral valve of the subject in a manner in which the first end of the structure is distanced from the second end of the structure, and
the implant structure in its implanted state defines a partial annuloplasty ring.

In an embodiment:
the apparatus is configured to be implanted along an annulus of a mitral valve of the subject,
the first portion of the implant structure is configured to be coupled to a first location along the annulus in a vicinity of a first trigone adjacent to the mitral valve, and
the second portion of the implant structure is configured to be coupled to a second location along the annulus in a vicinity of a second trigone adjacent to the mitral valve.

In an embodiment:
the implant structure is shaped to provide first and second ends in communication with the first and second portions, respectively,
the first end is configured to be coupled to the first location along the annulus in the vicinity of the first trigone adjacent to the mitral valve, and
the second end of the implant structure is configured to be coupled to the second location along the annulus in the vicinity of the second trigone adjacent to the mitral valve.

In an embodiment:
the first portion has first and second ends, the first end of the first portion being coupled to the spool, the second portion has first and second ends, the first end of the second portion being coupled to the spool, the apparatus includes first and second flexible members each having first and second ends, the first end of the first flexible member is coupled to the spool, and the second end of the first flexible member is coupled to the second end of the first portion, and the first end of the second flexible member is coupled to the spool, and the second end of the second flexible member is coupled to the second end of the first portion.

In an embodiment, in response to rotation of the spool in a first direction thereof, respective portions of the first and second flexible members are configured to be wound around the spool, and, responsively, to pull the respective second ends of the first and second flexible members toward the spool, and responsively to draw the first and second portions of the implant structure toward each other.

In an embodiment:

the apparatus is configured to be implanted along an annulus of a mitral valve of a heart of the subject, a first section of the implant structure is flexible and longitudinally compressible, and a second section in series with the first section of the implant structure, the second section being flexible and less longitudinally compressible than the first section.

In an embodiment, the second section is not longitudinally compressible.

In an embodiment, a radius of curvature at a center of the first section is smaller than a radius of curvature at a center of the second section, when no external force is applied to the implant structure.

In an embodiment, the second section of the implant structure has first and second ends thereof and a body portion disposed between the first and second ends, the second section of the implant structure being configured to be disposed along a portion of the annulus in a manner in which:

the first end of the second section is configured to be coupled to the annulus in a vicinity of a left trigone of the heart that is adjacent to a mitral valve of the subject, the second end of the second section is configured to be coupled to the annulus in a vicinity of a right trigone of the heart that is adjacent to the mitral valve, and the body portion is configured to be disposed along the annulus in a vicinity of the annulus that is between the left and right trigones.

In an embodiment, the body portion disposed between the first and second ends of the second section of the implant structure has a length of 10-50 mm.

In an embodiment, the apparatus is configured to be implanted along an annulus of a mitral valve of the subject in a manner in which the implant structure is formed into at least a portion of an annuloplasty ring.

In an embodiment, the apparatus includes a plurality of sutures, each suture of the plurality of sutures being configured to be fastened to a respective location along a circumference of the annulus of the subject, the plurality of sutures being configured to facilitate advancement of the implant structure toward the annulus.

In an embodiment, the plurality of sutures are configured to be coupled to the implant structure at respective locations thereof that are in parallel with the respective locations along the circumference of the annulus of the subject, and the implant structure is formed into the annuloplasty ring in response to the coupling.

In an embodiment, the implant structure is compressible along a longitudinal axis of the implant structure.

In an embodiment, the implant structure includes a coiled structure having a lumen thereof.

In an embodiment, the flexible member is disposed within the lumen of the coiled structure.

In an embodiment, in response to rotation of the spool, the flexible member is configured to longitudinally compress the implant structure.

In an embodiment, the apparatus includes a plurality of sutures configured to be coupled to an annulus of a mitral valve of the subject and to facilitate implantation of the implant structure along the annulus.

In an embodiment, the apparatus includes a plurality of anchors respectively coupled to the plurality of sutures and configured to be anchored to tissue of the annulus of the subject.

In an embodiment, the plurality of anchors are configured to lock the implant structure in place with respect to the annulus.

In an embodiment, the plurality of anchors are configured to be implanted along a circumference of the annulus, and to be coupled to the implant structure in a manner which forms the implant structure into a curved configuration.

In an embodiment:

the spool has a first end shaped to define a first opening, and a second end shaped to define a second opening, the spool being shaped to define a channel extending from the first opening to the second opening, the channel being configured for passage therethrough of an elongate tool, and the second end of the spool has a lower surface thereof shaped to:

provide at least a portion thereof having a circumference, and define one or more recesses at locations along the circumference.

In an embodiment, the apparatus includes a mechanical element having a planar surface coupled to the lower surface of the spool, the mechanical element being shaped to provide:

a protrusion protruding out of a plane of the planar surface of the mechanical element, the protrusion being disposed within one of the recesses during a resting state of the mechanical element, in a manner that restricts rotation of the spool, and a depressible portion coupled to the protrusion, the depressible portion being disposed in communication with the second opening of the lower surface, and configured to dislodge the protrusion from within the recess in response to a force applied thereto by the elongate tool.

In an embodiment:

the spool has a first end and a second end, the first end being shaped to receive a portion of a tool, and the first end of the spool has an upper surface thereof shaped to:

provide at least a portion thereof having a circumference, and define one or more recesses at respective locations along the circumference.

In an embodiment, the apparatus includes:

a mechanical element having a planar surface coupled to the upper surface of the spool, the mechanical element being shaped to provide at least one protrusion protruding out of a plane of the planar surface of the mechanical element, the protrusion being disposed within one of the recesses during a resting state of the mechanical element, in a manner that restricts rotation of the spool; and a compressible element coupled to the second end of the spool, the compressible element being configured to be compressed and facilitate dislodging of the protrusion from within the recess in response to a force applied to the spool by the elongate tool.

There is additionally provided, in accordance with an embodiment of the present invention, a method, including:

providing an implant structure having first and second portions thereof, the implant structure including:
a spool coupled to the implant structure in a vicinity of the first portion of the structure; and
a flexible member coupled at a first end thereof to the spool, and not coupled at a second end thereof to the spool;
advancing the implant structure, in a first configuration thereof, toward an annulus of the subject;
coupling the structure to the annulus; and
rotating the spool, and thereby:
winding a portion of the flexible member around the spool;
contracting the implant structure by pulling on the second end of the flexible member and thereby drawing the first and second portions of the implant structure toward each other; and
contracting the annulus.

In an embodiment, coupling the structure to the annulus includes:
coupling the structure to a mitral valve of the annulus;
coupling the first portion of the implant structure to a first location along the annulus in a vicinity of a first trigone adjacent to the mitral valve; and
coupling the second portion of the implant structure to a second location along the annulus in a vicinity of a second trigone adjacent to the mitral valve.

In an embodiment, advancing the implant structure includes transcatheterally advancing the implant structure.

In an embodiment, advancing the implant structure in the first configuration includes advancing the implant structure in a linear configuration thereof.

In an embodiment, contracting the implant structure includes rotating the spool in a first direction thereof, and the method further includes expanding the implant structure by rotating the spool in a second direction thereof that is opposite the first direction.

In an embodiment, advancing the implant structure in the first configuration includes forming the structure into a curved configuration and advancing the implant structure in the curved configuration thereof.

In an embodiment, advancing the implant structure in the first configuration includes forming the structure into a substantially closed curved configuration and advancing the implant structure in the closed curved configuration thereof.

In an embodiment, the method includes coupling a plurality of sutures to the annulus along at least a portion of a circumference thereof, and:
forming the structure into the curved configuration includes coupling the plurality of sutures to respective portions of the implant structure; and
advancing the implant structure in the curved configuration thereof includes advancing the implant structure along the plurality of sutures.

There is yet additionally provided, in accordance with an embodiment of the present invention apparatus, including:
a rotatable structure having a first end shaped to define a first opening, and a second end shaped to define a second opening, the rotatable structure being shaped to define a channel extending from the first opening to the second opening, the channel being configured for passage therethrough of an elongate tool, and the second end of the structure having a lower surface thereof shaped to:
provide at least a portion thereof having a circumference, and
define one or more recesses at locations along the circumference; and
a mechanical element having a planar surface coupled to the lower surface of the rotatable structure, the mechanical element being shaped to provide:
a protrusion protruding out of a plane of the planar surface of the mechanical element, the protrusion being disposed within one of the recesses during a resting state of the mechanical element, in a manner that restricts rotation of the rotatable structure, and
a depressible portion coupled to the protrusion, the depressible portion being disposed in communication with the second opening of the lower surface, and configured to dislodge the protrusion from within the recess in response to a force applied thereto by the elongate tool.

In an embodiment, the rotatable structure includes a spool, and the apparatus further includes a flexible member configured to be coupled at at least a first end thereof to the spool and to be wrapped around the spool in response to rotation thereof.

In an embodiment, the apparatus further includes an implant, and:
the spool is coupled to at least a portion of the implant,
and the flexible member is disposed in communication with the implant and coupled at at least a first end thereof to the spool, and
in response to rotation of the spool in a first direction thereof, the flexible member is configured to be wound around the spool, and, responsively, to contract the implant.

In an embodiment, the flexible member is configured to be unwound from around the spool and to facilitate expansion of the implant in response to rotation of the spool in a second direction thereof that is opposite the first direction.

In an embodiment, a second end of the flexible member is not coupled to the spool.

In an embodiment, the implant includes a compressible element shaped to define a lumen thereof, and the flexible member is disposed within the lumen of the compressible element.

There is further provided, in accordance with an embodiment of the present invention, an annuloplasty structure configured for implantation along an annulus of a mitral valve of a heart of a subject, the structure including:
a first portion that is flexible and longitudinally compressible; and
a second portion in series with the first portion, the second portion being flexible and less longitudinally compressible than the first portion, and having first and second ends thereof and a body portion between the first and second ends, the annuloplasty structure being configured for implantation along the annulus in a manner in which:
the first end of the second portion is configured to be coupled to the annulus in a vicinity of a left trigone adjacent to the mitral valve,
the second end of the second portion is configured to be coupled to the annulus in a vicinity of a right trigone adjacent to the mitral valve, and
the body portion of the second portion is configured to be disposed along the annulus in a vicinity of the annulus that is between the left and right trigones.

In an embodiment, the body portion is not compressible.

In an embodiment, the body portion disposed between the first and second ends of the second portion has a length of 10-50 mm.

There is yet further provided, in accordance with an embodiment of the present invention, a method, including:
providing an annuloplasty structure having:
a first portion that is flexible and longitudinally compressible; and a second portion in series with the first portion, the second portion being flexible and less longitudinally compressible than the first portion, and having first and second ends thereof and a body portion disposed between the first and second ends;

implanting the annuloplasty structure along an annulus of a valve of a subject by:

coupling the first end of the second portion to the annulus in a vicinity of a left trigone adjacent to the valve;

coupling the second end of the second portion the annulus in a vicinity of a right trigone adjacent to the valve; and coupling the body portion of the second portion along the annulus in a vicinity of the annulus that is between the left and right trigones; and compressing the first portion of the annuloplasty structure while substantially not compressing the second portion of the annuloplasty structure.

In an embodiment, providing the annuloplasty ring including providing an annuloplasty ring having a radius of curvature at a center of the first portion is smaller than a radius of curvature at a center of the second portion, when no external force is applied to the annuloplasty structure.

In an embodiment, providing the annuloplasty structure includes providing a closed annuloplasty ring.

In an embodiment, providing the annuloplasty structure includes providing a partial annuloplasty ring.

In an embodiment, attaching the second end of the second portion the annulus including attaching the second end of the second portion the annulus at a distance between from the first end of between 10 and 50 mm.

There is also provided, in accordance with an embodiment of the present invention, apparatus, including:

a rotatable structure having a first end and a second end, the first end being shaped to receive a portion of a tool and having an upper surface thereof shaped to:

provide at least a portion thereof having a circumference, and define one or more recesses at respective locations along the circumference;

a mechanical element having a planar surface coupled to the upper surface of the rotatable structure, the mechanical element being shaped to provide at least one protrusion protruding out of a plane of the planar surface of the mechanical element, the protrusion being disposed within one of the recesses during a resting state of the mechanical element, in a manner that restricts rotation of the rotatable structure; and a compressible element coupled to the second end of the rotatable structure, the compressible element being configured to be compressed and facilitate dislodging of the protrusion from within the recess in response to a force applied to the rotatable element by the elongate tool.

In an embodiment, the rotatable structure includes a spool, and the apparatus further includes a flexible member configured to be coupled at at least a first end thereof to the spool and to be wrapped around the spool in response to rotation thereof.

In an embodiment, the apparatus includes an implant, and: the spool is coupled to at least a portion of the implant, and the flexible member is disposed in communication with the implant and coupled at at least a first end thereof to the spool, and in response to rotation of the spool in a first direction thereof, the flexible member is configured to be wound around the spool, and, responsively, to contract the implant.

In an embodiment, the flexible member is configured to be unwound from around the spool and to facilitate expansion of the implant in response to rotation of the spool in a second direction thereof that is opposite the first direction.

In an embodiment, a second end of the flexible member is not coupled to the spool.

In an embodiment, the implant includes a compressible element shaped to define a lumen thereof, and the flexible member is disposed within the lumen of the compressible element. The present invention will be more fully understood from the following detailed description of embodiments thereof, taken together with the drawings, in which:

BRIEF DESCRIPTION OF THE DRAWINGS

FIG. 1 is a schematic illustration of an annuloplasty structure in a resting state thereof, in accordance with an embodiment of the present invention;

FIGS. 2-3 are schematic illustrations of the annuloplasty structure in respective contracted states thereof, in accordance with an embodiment of the present invention;

FIG. 5 is a schematic illustration of the annuloplasty structure, in accordance with another embodiment of the present invention;

FIGS. 6A-B, 7, and 8A-B are schematic illustrations of the contracting mechanism that is used to contract the annuloplasty structure, in accordance with an embodiment of the present invention;

FIGS. 9-11, 12A-B, and 13 are schematic illustrations of a method for implanting the annuloplasty structure of FIGS. 1-4, in accordance with an embodiment of the present invention;

DETAILED DESCRIPTION OF THE INVENTION

Figure 4:
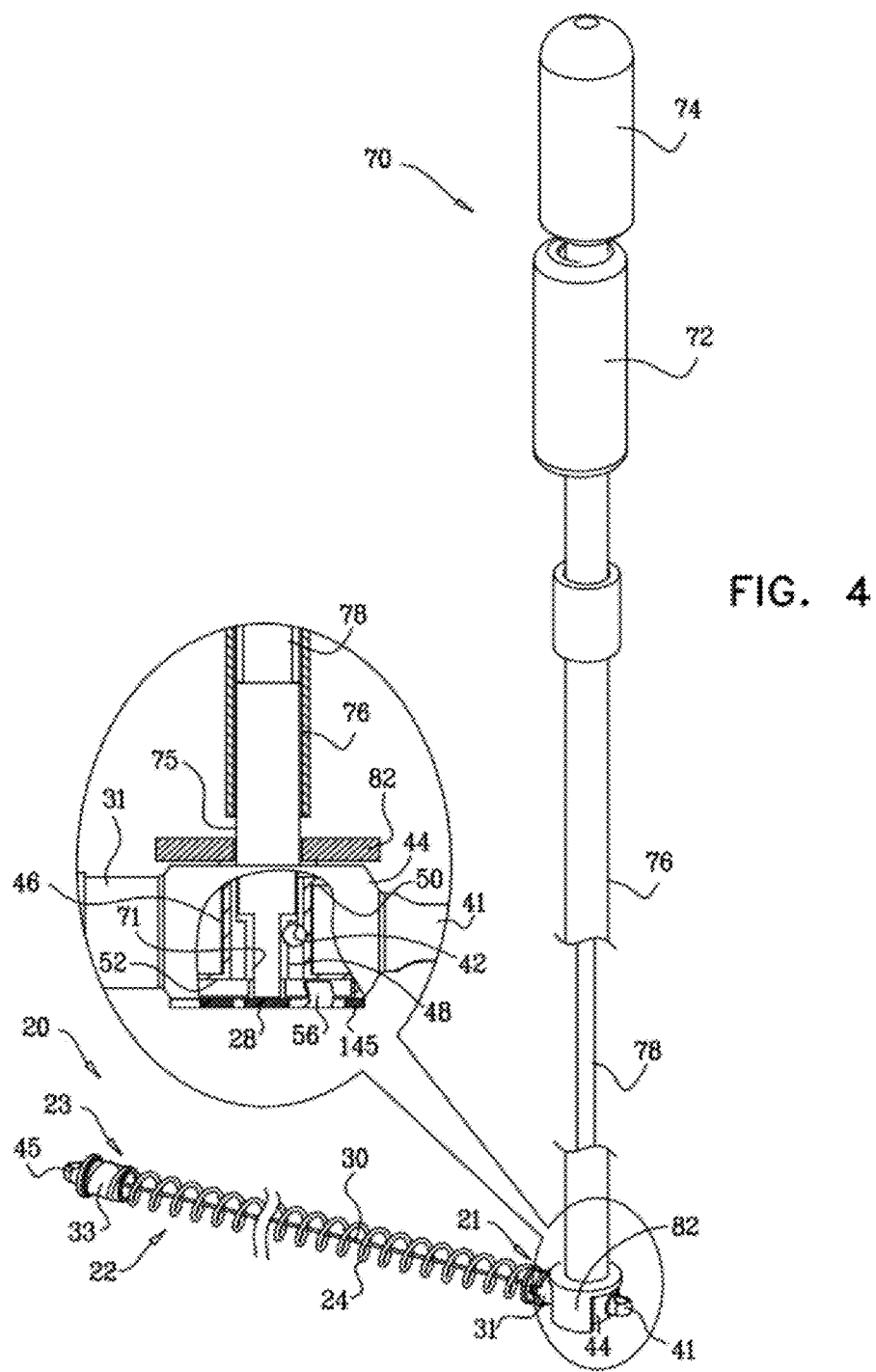
FIG. 4 is a schematic illustration of the annuloplasty structure of FIG. 1 being coupled to an elongate tool, in accordance with an embodiment of the present invention.

Reference is now made to FIGS. 1-3, which are schematic illustrations of a system 20 for repairing a dilated annulus of a subject comprising an implant structure, e.g., an annuloplasty structure 22, comprising a body portion 24, a flexible member 30, and a contracting mechanism 40, in accordance with an embodiment of the present invention. FIG. 1 shows structure 22 in a resting state thereof in which structure 22 defines a linear, elongate structure having a longitudinal axis thereof. At least a portion, e.g., the entirety, of body portion 24 comprises a compressible material, e.g., a coiled element, as shown by way of illustration and not limitation. For example, body portion 24 may comprise stent-like struts, or a braided mesh. Typically, body portion 24 defines a lumen along the longitudinal axis of structure 22 which houses flexible member 30. Flexible member 30 comprises a wire, a ribbon, a rope, or a band, comprising a flexible metal. Flexible member 30 is coupled at a first end thereof to contracting mechanism 40 which is coupled to a first end 21 of structure 22. A second end of flexible member 30 is coupled to a second end 23 of structure 22. Typically, during the resting state, flexible member 30 is disposed in parallel with the longitudinal axis of structure 22.

Typically, body portion 24 comprises a biocompatible material, e.g., nitinol, stainless steel, platinum iridium, titanium, expanded polytetrafluoroethylene (ePTFE), or cobalt chrome. In some embodiments, body portion 24 is coated with PTFE (Polytetrafluoroethylene). In some embodiments, body portion 24 comprises accordion-like compressible structures which facilitate proper cinching of the annulus when structure 22 is contracted. Body portion 24, when compressed, e.g., typically along a longitudinal axis of structure 22, enables portions of annuloplasty structure 22 to contract and independently conform to the configuration of the annulus of the mitral valve of a given subject. Thus, the compressible element of body portion 24 facilitates contraction of the annulus in response to contraction of structure 22.

Typically, flexible member 30 comprises a flexible and/or superelastic material, e.g., nitinol, polyester, stainless steel, or cobalt chrome, and is configured to reside chronically within structure 22. In some embodiments, flexible member 30 comprises a braided polyester suture (e.g., Ticron). In some embodiments, flexible member 30 is coated with polytetrafluoroethylene (PTFE). In some embodiments, flexible member 30 comprises a plurality of wires that are intertwined to form a rope structure.

Contracting mechanism 40 comprises a housing 44 which houses a rotatable structure, or a spool 46. Spool 46 has a cylindrical body that is disposed perpendicularly with respect to the longitudinal axis of structure 22. As shown in FIG. 2, spool 46 is shaped to provide a hole 42 for coupling of the first end of flexible member 30 thereto and, thereby, to contracting mechanism 40. Spool 46 is shaped to define a channel 48 which extends through the cylindrical portion of spool 46 from an opening provided by an upper surface 50 of spool 46 to an opening provided by a lower surface 52 of spool 46. Channel 48 provides a lumen which is disposed along an axis that is perpendicular to the longitudinal axis of structure 22 in its elongate, linear configuration. As described hereinbelow, a distal portion of a screwdriver engages spool 46 via channel 48 and rotates spool 46 in response to a rotational force applied to the screwdriver. The rotational force applied to the screwdriver rotates spool 46 via the portion of the screwdriver that is disposed within channel 48 of spool 46.

FIG. 2 shows partial contraction of structure 22 in response to a rotational force applied to spool 46. In response to the rotational force, a portion of flexible member 30 is wrapped around spool 46, as shown in the enlarged image of FIG. 2. As flexible member 30 is wrapped around spool 46, the second end of member 30 is pulled toward contracting mechanism 40 in the direction as indicated by the arrow. Pulling the second end of flexible member 30 toward mechanism 40 pulls second end 23 of structure 22 toward first end 21 of structure 22, in the direction as indicated by the arrow. Responsively, the compressible element of body portion 24 is longitudinally compressed, thereby contracting structure 22.

It is to be noted that the linear structure 22 contracts to form a curved structure 22, as shown, by way of illustration and not limitation. In some embodiments, contraction of structure 22 forms the structure into a curved configuration. Alternatively, structure 22 is made to assume the curved configuration prior to contracting thereof, and during the contracting, the curved structure is contracted. That is, without being formed into a curved configuration prior to the contracting, structure 22 is compressed linearly along the longitudinal axis thereof.

In some embodiments, the contracting of structure 22 enables structure 22 to assume the configuration shown. Alternatively, or additionally, prior to contraction, structure 22 is anchored, or otherwise fastened, at least in part to the annulus of the valve of the subject at respective locations along structure 22. The anchoring, or otherwise fastening, of structure 22 to the annulus enables structure 22 to assume the configuration shown, as described hereinbelow.

FIG. 3 shows further contraction of structure 22 in response to continued rotation of spool 46. As shown in the enlarged image of FIG. 3, a larger portion of flexible member 30 is wrapped around spool 46 (i.e., member 30 is looped many times around element 46), as compared with the portion of flexible member 30 that is wrapped around spool 46 (as shown in the enlarged image of FIG. 2). Responsively to the wrapping of flexible member 30 around spool 46, the compressible element of body portion 24 is further longitudinally compressed, and structure 22 is further contracted. As such, structure 22 provides an adjustable partial annuloplasty ring.

Reference is now made to FIGS. 1-3. First end 21 of structure 22 comprises a coupling member 31 which couples a first end of body portion 24 to contracting mechanism 40. Typically, the first end of body portion 24 is welded to coupling member 31. Contracting mechanism 40 is coupled to a first suture fastener 41 that is shaped to define a hole 43 for passage therethrough of a suture. Second end 23 of structure 22 comprises a second suture fastener 45 that is shaped to define a hole 47 for passage therethrough of a suture. Second end 23 of structure 22 comprises a coupling member 33 which couples a second end of body portion 24 to suture fastener 45. Typically, the second end of body portion 24 is welded to coupling member 33.

Reference is now made to FIG. 4, which is a schematic illustration of system 20 comprising an elongate tool 70 that is reversibly coupled to contracting mechanism 40 of structure 22, in accordance with an embodiment of the present invention. Tool 70 comprises an elongate body portion 76 which houses a flexible rod 78 that is coupled at a distal end thereof to a screwdriver head 75. Typically, rod 78 functions as a screwdriver which applies force to screwdriver head 75 (that is disposed within channel 48 of spool 46) in order to rotate spool 46, and thereby facilitate contraction of structure 22. A proximal portion of tool 70 comprises rotatable structures 72 and 74 which rotate with respect to each other and cause flexible rod 78 to rotate with respect to body portion 76.

(In this context, in the specification and in the claims, "proximal" means closer to the orifice through which tool 70 is originally placed into the body of the subject, and "distal" means further from this orifice.)

In some embodiments, tool 70 is coupled to an annuloplasty sizer and the annuloplasty structure is wrapped around at least a portion of the sizer. Once wrapped around the sizer, the flexible member is contracted such that the annuloplasty structure hugs and is stabilized around the sizer. The sizer helps position the annuloplasty structure along the annulus and stabilize the structure as it is being contracted.

Typically, tool 70 facilitates the advancement of structure 22 and subsequent contraction thereof. The distal portion of tool 70 comprises a housing 82 which surrounds housing 44 of structure 22 and stabilizes housing 44 during the advancement and contraction of structure 22. Flexible rod 78 is coupled at a distal end thereof to screwdriver head 75. Screwdriver head 75 is shaped to define a distal protrusion 71 which is disposed within channel 48 of spool 46 during the advancement of structure 22 toward the annulus of the subject, and during the contraction of structure 22.

In some embodiments, an advancement tool other than tool 70 is used to facilitate advancement of structure 22 toward the annulus. Following coupling of structure 22 to the annulus, the advancement tool is decoupled from structure 22 and extracted from within the body of the subject. Subsequently, tool 70 may be advanced toward housing 44 of structure 22 and facilitate contraction of structure 22. In such an embodiment, the advancement tool may be coupled at a distal end thereof to an annuloplasty sizer and structure 22 is tightened around the sizer during the advancement of structure 22 toward the annulus.

A distal portion of protrusion 71 rests against a depressible portion 28 of a locking mechanism 145. Typically, locking mechanism 145 comprises a mechanical element having a planar surface that is coupled to spool 46. In some embodiments, at least a portion of mechanism 145 is coupled to, e.g., soldered to, housing 44. Typically, lower surface 52 of spool 46 is shaped to define one or more (e.g., a plurality, as shown) of recesses, e.g., holes (not shown for clarity of illustration). Locking mechanism 145 is shaped to provide a protrusion 56 which protrudes out of the plane of the planar surface of the mechanical element of mechanism 145 and into one of the recesses of lower surface 52 of spool 46, as described hereinbelow.

It is to be noted that the planar, mechanical element of locking mechanism 145 is shown by way of illustration and not limitation and that any suitable mechanical element having or lacking a planar surface but shaped to define at least one protrusion may be used together with locking mechanism 145.

The enlarged image in FIG. 4 shows a cross-section of spool 46 and locking mechanism 145 in a resting state thereof in which protrusion 56 of locking mechanism 145 is disposed within one of the recesses of lower surface 52 of spool 46. In such a configuration, protrusion 56 locks in place spool 46 and restricts rotation thereof.

Protrusion 56 remains disposed within the recess of lower surface 52 of spool 46 until a force is applied to locking mechanism 145 which causes protrusion 56 to be dislodged from within the recess of lower surface 52 of spool 46. Typically, protrusion 56 is coupled to depressible portion 28 of locking mechanism 145. As described hereinbelow, tool 70 is pushed distally causes protrusion 71 of screwdriver head 75 to press down on depressible portion 28. As a result, protrusion 56 of locking mechanism 145 is pushed down together with depressible portion 28, and is thereby dislodged from within the recess of lower surface 52 of spool 46.

Once spool 46 is released from protrusion 56 of locking mechanism 145, flexible rod 78 of tool 70 is rotated in order to rotate screwdriver head 75, and thereby spool 46.

Typically, housing 82 of tool 70 functions to provide a reference force against housing 44 of structure 22 during the rotation of rotating element 46.

Tool 70 may be used in order to advance structure 22 toward the annulus in an open heart procedure, minimally-invasive procedure, and/or in a transcatheter procedure. For embodiments in which tool 70 is used during a transcatheter procedure, tool 70 comprises a substantially longer, more flexible body portion than if used during an open-heart or minimally-invasive procedure. In some embodiments, tool 70 is used to advance structure 22 toward the annulus in a linear configuration (as shown), in a curved configuration (i.e., in a manner in which structure 22 defines an annuloplasty band or a partial annuloplasty ring), or in a closed configuration (i.e., a configuration in which second end 23 of structure 22 is coupled to housing 44 such that structure 22 defines an annuloplasty ring).

FIG. 5 shows a system 120 for repairing a dilated annulus of a subject comprising an annuloplasty structure 122 that defines an annuloplasty ring, in accordance with an embodiment of the present invention. Annuloplasty structure 122 comprises first and second ends 21 and 23, respectively, which are coupled to (e.g., welded to) a housing 144 that houses contracting mechanism 40. Housing 144 is shaped to provide first and second coupling members 31 and 35 which are coupled to first and second ends 21 and 23, of structure 122, respectively.

In some embodiments structure 122 comprises a linear, elongate structure in a resting configuration thereof. Prior to implantation, first and second ends 21 and 23 of structure 122 are welded or otherwise attached to coupling members 31 and 35, respectively, thereby facilitating the formation of structure 122 into a substantially ring-shaped structure. As described hereinabove with respect to structure 22 with reference to FIGS. 1-3, structure 122 comprises a body portion 24 defining a lumen for housing flexible member 30. Typically, body portion 24 comprises a compressible element. As described hereinabove, a first end of flexible member 30 is coupled to contracting mechanism 40, while a second end of flexible member 30 is coupled to second end 23 of structure 122.

It is to be noted that for some embodiments, flexible member 30 may be coupled at both its first and second ends to spool 46 of contracting mechanism 40. In some embodiments, a first end of flexible member 30 is coupled to spool 46 while a second end of flexible member 30 is coupled to the housing which houses spool 46.

As shown, structure 122 defines a substantially ring-shaped configuration, e.g., a "D"-shaped configuration, as shown, which conforms to the shape of the annulus of a mitral valve of the subject. Prior to contracting of structure 122, the compressible element of body portion 24 is relaxed and structure 122 defines a first perimeter thereof. Structure 122 provides portions 49 which comprise a material in a configuration in which portions 49 are flexible and less longitudinally compressible, e.g., not longitudinally compressible, with respect to the compressible element of body portion 24. Portions 49 are configured to be disposed along the fibrous portion of the annulus that is between the trigones of the mitral valve of the heart when structure 122 is anchored, sutured, fastened or otherwise coupled to the annulus of the mitral valve. Portions 49 impart rigidity to structure 122 in the portion thereof that is disposed between the fibrous trigones such that structure 122 better mimics the conformation and functionality of the mitral valve.

Typically, both portions 49 have a combined length of 10-50 mm.

Thus, structure 122 defines a compressible portion and a non-compressible portion. Typically, a radius of curvature at a center of the compressible portion of body portion 24 is smaller than a radius of curvature at a center of less-compressible portions 49, when no external force is applied to the annuloplasty structure.

It is to be noted that the compressible element of body portion 24 and less-compressible portions 49 comprise coiled elements by way of illustration and not limitation. For example, the compressible element of body portion 24 and less-compressible portions 49 may comprise stent-like struts, or a braided mesh. In either configuration, portions 49 are chronically longitudinally compressed in a resting state of structure 122.

Housing 82 of tool 70 is coupled to structure 122 by surrounding housing 144. Tool 70 facilitates contracting of structure 122 via contracting mechanism 40 in a manner as described hereinabove with respect to the contracting of structure 22 with reference to FIGS. 1-4. Tool 70 is shown as comprising a coupling element 77 which couples screwdriver head 75 to flexible rod 78.

Reference is again made to FIG. 5. It is to be noted that, structure 122 may be provided independently of less-compressible portions 49. In such an embodiment, the annuloplasty structure comprises a fully compressible ring, e.g., a continuous ring.

Reference is again made to FIG. 5. It is to be noted that housing 144 may be disposed at any suitable location along structure 122, and not only in between portions 49. For example, housing 144 may be coupled to the section of body portion 24 that is compressible. In some embodiments, housing 144 may be disposed in the middle of the section of body portion 24 that is compressible. In some embodiments, housing 144 may be coupled to structure 122 at an interface between a first end of portion 49 and the section of body portion 24 that is compressible. In such an embodiment portions 49 may be combined to form one substantially less-compressible portion having first and second ends that are in series with the compressible portion of body portion 24.

FIGS. 6A-B show a relationship between individual components of contracting mechanism 40, in accordance with an embodiment of the present invention. As shown, housing 144 is shaped to provide coupling members 31 and 35 for coupling first and second ends of the annuloplasty structure thereto. Contracting mechanism 40 is shown as comprising housing 144, by way of illustration and not limitation. For embodiments in which mechanism 40 comprises housing 44 (described hereinabove with reference to FIGS. 1-4), housing 44 comprises only coupling member 31 on one side, and a suture fastener on the other side of housing 44.

Spool 46 is configured to be disposed within housing 144 and defines an upper surface 50, a lower surface 52 and a cylindrical body portion disposed vertically between surfaces 50 and 52. Spool 46 is shaped to provide channel 48 which extends from an opening provided by upper surface 50 to an opening provided by lower surface 52. The cylindrical body portion of spool 46 is shaped to define a hole 42. Typically, flexible member 30 is coupled to spool 46 via hole 42. In some embodiments, flexible member 30 comprises a continuous ring-shaped band which passes through hole 42 of spool 46.

Lower surface 52 of spool 46 is shaped to define one or more (e.g., a plurality, as shown) recesses 54 disposed between portions 55 of lower surface 52. Although four recesses 54 are shown by way of illustration and not limitation, it is to be noted that any suitable number of recesses 54 may be provided, e.g., between 1 and 10 recesses. It is to be noted that four recesses 54 are shown by way of illustration and not limitation and that any suitable number of recesses 54 may be provided.

Locking mechanism 145 is coupled to lower surface 52. In some embodiments, at least a portion of locking mechanism 145 is welded to housing 144. Typically, locking mechanism 145 defines a mechanical element having a planar surface that has at least one slit 58. Locking mechanism 145 is shaped to provide a protrusion 56 which projects out of a plane defined by the planar surface of the mechanical element. Slit 58 defines a depressible portion 28 of locking mechanism 145 that is disposed in communication with protrusion 56. Depressible portion 28 is moveable in response to a force applied thereto typically by tool 70, as described hereinabove, and as shown in detail hereinbelow with reference to FIGS. 8A-B.

Reference is now made to FIGS. 6A-B. It is to be noted that locking mechanism 145 may be coupled to housing 44 as described hereinabove with reference to FIGS. 1-4.

Figure 7:
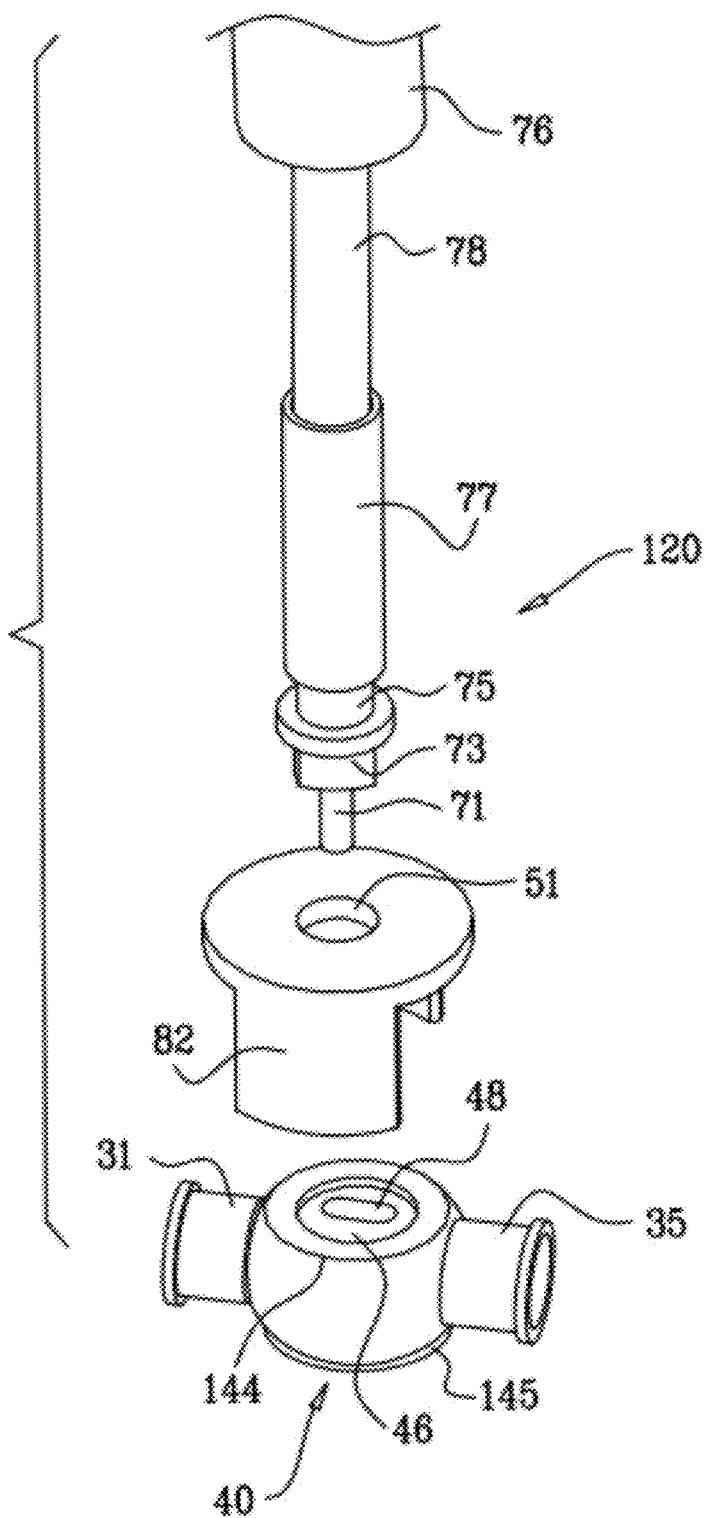

FIG. 7 is a schematic illustration contracting mechanism 40 and components of tool 70 that is configured to be coupled to contracting mechanism 40, in accordance with an embodiment of the present invention. Tool 70 comprises body 76, e.g., a sleeve, and a flexible, rotatable rod 78 disposed within a sleeve provided by body 76. A coupling element 77 couples screwdriver head 75 to flexible rod 78. Typically, screwdriver head 75 is shaped to define a proximal cylindrical structure which is housed within a lumen provided by coupling element 77. A distal end of screwdriver head 75 is shaped to define a distal insert portion 73 which is designated for insertion within channel 48 of spool 46. Housing 82 is coupled to a distal end of tool 70 and functions as a cage which surrounds housing 144. Typically, during rotating of spool 46 by tool 70, housing 82 provides a reference force which facilitates the applying of a force to spool 46 by tool 70.

Following sufficient contraction of the annuloplasty structure, tool 70 and housing 82 are disengaged from housing 144 of the annuloplasty structure and are extracted from within the heart of the subject.

FIGS. 8A-B are schematic illustrations of the locking and unlocking of spool 46, in accordance with an embodiment of the present invention. FIG. 8A shows contracting mechanism 40 in a locked configuration in which protrusion 56 of locking mechanism 145 is disposed within a recess 54 of lower surface 52 of spool 46. FIG. 8B shows the unlocking of spool 46 by the dislodging of protrusion 56 from recess 54 of spool 46.

Reference is now made to FIGS. 6A-B, 7, and 8A-B. During a resting state of the locking mechanism, depressible portion 28 is disposed perpendicularly with respect to a longitudinal axis of channel 48, and protrusion 56 is disposed within one of recesses 54 and thereby locks spool 46 in place with respect to housing 144 such that rotation of spool 46 is restricted (FIG. 8A). In the resting state of locking mechanism 145, the distal portion of protrusion 71 of screwdriver head 75 rests against depressible portion 28 of locking mechanism 145.

FIG. 8B shows screwdriver head 75 of tool 70 applying a pushing force to locking mechanism 145 (in the direction as indicated by the arrow). The pushing force pushes downward protrusion 71 of screwdriver head 75 such that protrusion 71 pushes downward depressible portion 28, e.g., typically at a non-zero angle with respect to spool 46. Pushing portion 28 downward pushes downward protrusion 56 such that it is dislodged from within recess 54 of spool 46, and, thereby unlocking spool 46. Following the unlocking, tool 70 facilitates the rotation of screwdriver head 75 in order to rotate spool 46.

Channel 48 of spool 46 is shaped to accommodate the dimensions of insert 73 and protrusion 71 of screwdriver head 75. Insert 73 is shaped to provide an upper portion having a width that is wider than the protrusion 71 coupled thereto. In turn, channel 48 of spool 46 is shaped to accommodate insert 73 and protrusion 71 by defining an upper portion and a lower portion thereof in which the upper portion of channel 48 is wider than the lower portion. The narrower lower portion of channel 48 ensures that protrusion 71 is not advanced distally beyond a certain point as the narrower lower portion of channel 48 restricts passage therethrough of the upper, wider portion of insert 73.

It is to be noted that housing 144 and structure 122 are shown in FIGS. 6A-B, 7, and 8A-B by way of illustration and not limitation, and that embodiments described herein may be practiced in combination with housing 44 and/or structure 22.

Reference is again made to FIGS. 6A-B, 7, and 8A-B. Following rotation of spool 46 by tool 70, insert 73 of tool 70 is removed from within channel 48 spool 46 by pulling on tool 70, and depressible portion 28 returns to its resting state, i.e., perpendicular with respect to the longitudinal axis of channel 48. As depressible portion 28 returns to its resting state, protrusion 56 is introduced within one of the plurality of recesses 54 of lower surface 52 of spool 46 and thereby restricts rotation of spool 46.

It is to be noted that an outer sheath surrounds screwdriver portion 75 of tool 70 in FIGS. 8A-B. Screwdriver portion 75 is shaped to define a ring-shaped portion at a portion thereof that is disposed adjacently to housing 144. The ring-shaped portion has a diameter that is larger than the diameter of the opening provided by housing 144, and therefor is restricted from passage through housing 144. By pushing on tool 70, the ring shaped portion pushes against housing 144 in order to push the annuloplasty structure away from tool 70. As screwdriver portion 75 pushes against housing 144, the outer sheath is pulled proximally in order to pull tool 70 away from the annuloplasty structure.

Figure 9:
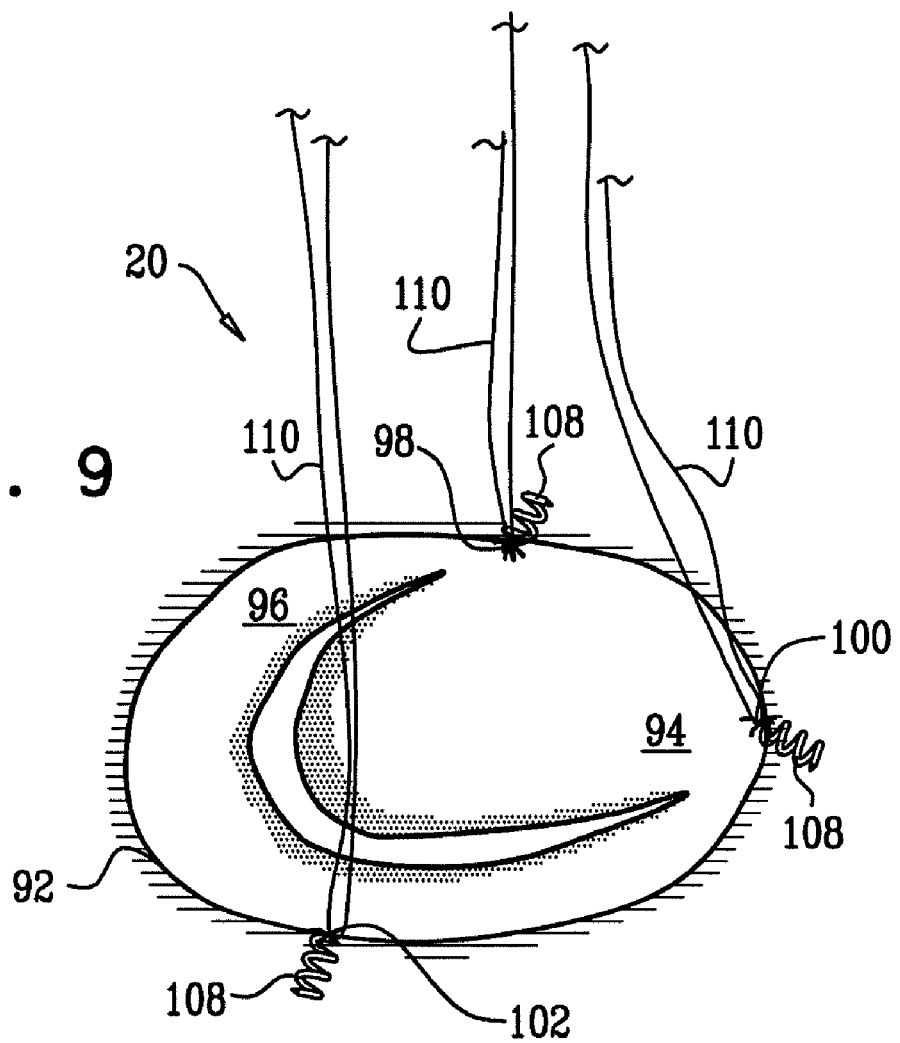

Reference is now made to FIGS. 9-11, 12A-B, and 13, which are schematic illustrations of a method for implantation of structure 22 of system 20 along an annulus 92 of the mitral valve of the subject, in accordance with an embodiment of the present invention. Typically, prior to advancement of the annuloplasty structure toward the annulus, a plurality of sutures are sutured, anchored, fastened, or otherwise coupled around the annulus. Typically, the sutures are accessible from a site outside the body of the subject. FIG. 9 shows a plurality of sutures 110, e.g., metal or fabric such as polyester, that are coupled via respective anchors 108 to respective locations 98, 100, and 102 along annulus 92 of the mitral valve. The dilated mitral valve is shown as having anterior leaflet 94 and posterior leaflet 96. Typically, each suture 110 is coupled to a respective helical anchor 108. As shown, sutures 110 are looped around a portion of anchors 108. In some embodiments, sutures 110 may be coupled at respective distal ends thereof to respective anchors 108. Anchors 108 are corkscrewed into tissue of annulus 92, thereby indirectly coupling sutures 110 to annulus 92.

Typically, during transcatheter procedures, sutures 110 are anchored to annulus 92, as shown in FIG. 9. It is to be noted that sutures 110 may be anchored to the annulus, as shown, during open-heart or minimally-invasive procedures.

It is to be noted that sutures 110 are anchored at locations 98, 100, and 102 by way of illustration and not limitation, and that sutures 110 may be anchored or otherwise fastened to any suitable location along annulus 92. Furthermore, it is to be noted that any suitable number of sutures 110 may be anchored or otherwise fastened to annulus 92, in accordance with the size of the dilated mitral valve of the subject. For example, between 2 and 20 sutures, typically between 2 and 14 sutures, may be anchored to annulus 92 via respective helical anchors 108.

During open-heart or minimally-invasive procedures to repair the dilated mitral valve, sutures 110 may be sutured directly to annulus 92 using techniques known in the art. Typically, a plurality of sutures are sutured along the entire circumference of the annulus in accordance with the size of the dilated annulus. In some embodiments, adjacently-disposed sutures may overlap in part. In some embodiments, the sutures are sutured to annulus in a manner in which the suture defines a portion disposed in the tissue, and first and second portions extending from either side of the portion of the suture that is disposed within the tissue. In such an embodiment, the suture may be sutured to the tissue in a manner in which the first and second portions of the tissue are disposed at a distance, e.g., 4 mm, from each other.

Figure 10:
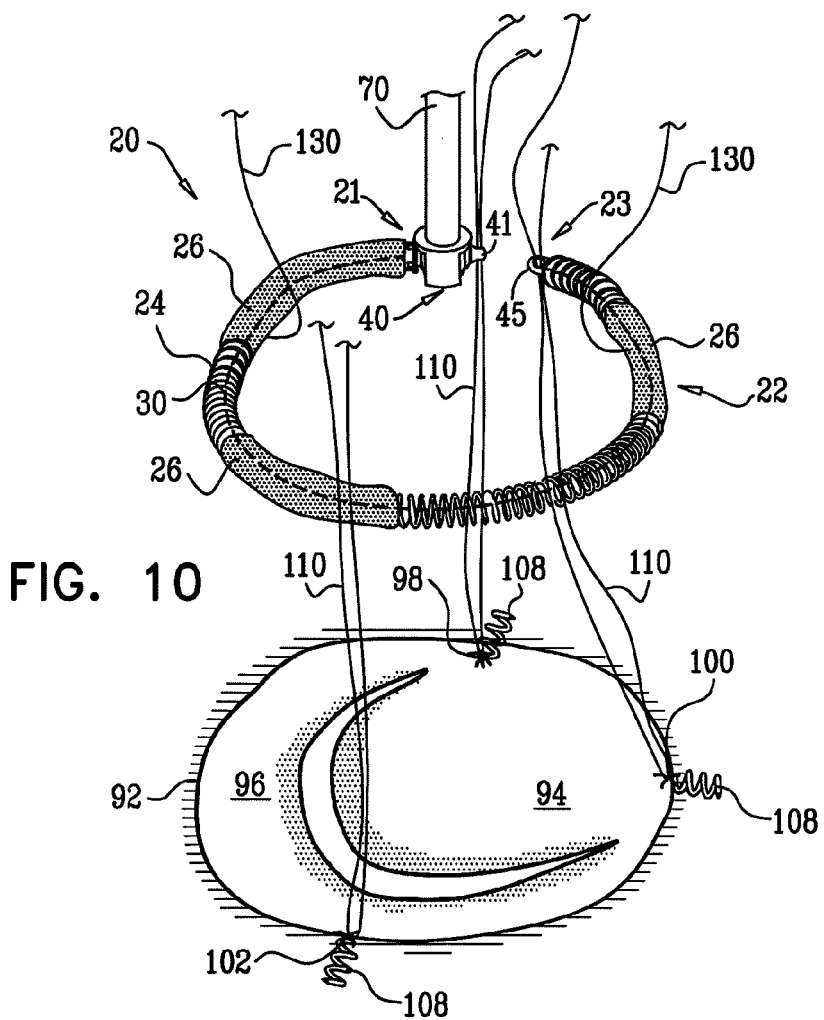

FIG. 10 shows the advancement of structure 22 along sutures 110 and toward annulus 92. Structure 22 is shown as comprising body portion 24 which houses flexible member 30 and is surrounded by a braided mesh 26 (for clarity of illustration, portions of body portion 24 are shown as not being surrounded by mesh 26). Typically, body portion 24 comprises a compressible element, as described herein. Typically, braided mesh 26 comprises a flexible material, e.g., metal or fabric such as polyester, and is longitudinally compressible. Typically, body portion 24 comprises a compressible element. Mesh 26 compresses responsively to the compression of the compressible element of body portion 24.

Prior to advancement toward annulus 92, structure 22 is coupled to tool 70, as described hereinabove. For embodiments in which structure 22 is transcatheterally implanted along annulus 92, structure 22 may be advanced linearly through the advancement catheter and pushed therethrough by tool 70. Typically, the advancement catheter is transseptally advanced toward the left atrium of the heart of the subject and tool 70 is advanced through the catheter.

In some embodiments, structure 22 may be coupled at respective ends thereof to housing 44 of contracting mechanism 40 such that structure 22 is advanced in a closed, substantially ring-shaped configuration. For embodiments in which structure 22 is transcatheterally advanced in a closed configuration, structure 22 may be folded, or otherwise collapsed, such that it fits within the lumen of the advancement catheter.

As shown in FIG. 10, prior to advancement of structure 22 toward the annulus, sutures 110 are threaded through respective portions of structure 22. Suture 110 that is sutured to location 98 of annulus 92 is threaded through suture fastener 41. Suture 110 that is sutured to location 100 is threaded through suture fastener 45. Suture 110 that is sutured to location 102 is threaded through mesh 26 at a portion along structure 22 that is between ends 21 and 23. Since locations 98, 100, and 102 are provided circumferentially with respect to annulus 92, following the threading of sutures 110 through structure 22, structure 22 is shaped (from its original linear configuration as shown in FIGS. 1 and 4) into a substantially circular, or curved, configuration, as shown, as it is advanced toward annulus 92. In some embodiments, structure 22 comprises a shape-memory alloy, e.g., nitinol, which enables structure 22 go assume the configuration as shown, independently of the threading therethrough of sutures 110.

Typically, each suture defines a portion that is looped around a portion of a respective anchor 108, and first and second portions extending from the looped portion. Respective ends of the first and second portions of each suture 110 are accessible from outside the body of the subject. As shown, the two portions of sutures 110 may be threaded through fasteners 41 and 45 and through mesh 26. Alternatively, a first portion of each suture 110 may be threaded through a respective hole defined by fasteners 41 and 45 and through mesh 26 while a second portion of each suture 110 may be threaded around respective fasteners 41 and 45 and around mesh 26. In such an embodiment, following the positioning of structure 22 along annulus 92, the first and second portions of sutures 110 are tied together around fasteners 41 and 45, and around mesh 26.

Typically, locations 98 and 100 are by way of illustration and not limitation, on or adjacently to the trigones of the heart that are near the mitral valve. Thus, first and second ends 21 and 23 of structure 22 will be disposed on or adjacently to the trigones. In such an embodiment a portion of structure 22 is not disposed in an area between the fibrous trigones. In some embodiments, respective portions of body portion 24 that are disposed adjacently to first and second ends 21 and 23 of structure 22 are less compressible, e.g., not compressible, as compared to the compressible element of body portion 24.

It is to be noted that first and second ends 21 and 23 of structure 22 are disposed in respective vicinities of the left and right trigones by way of illustration and not limitation, and that respective ends 21 and 23 may be coupled to any suitable portion along the annulus. That is, annuloplasty structure 22 may be coupled along the annulus in any suitable orientation and at any suitable location along the annulus.

Structure 22 is coupled to sutures 130, e.g., metal or fabric, at distal ends thereof. As described hereinbelow, sutures 130 facilitate the advancement of respective anchors toward structure 22 following its initial anchoring to annulus 92 via sutures 110. It is to be noted that only two sutures 130 are coupled to structure 22 by way of illustration and not limitation, and that any suitable number of sutures 130 may be coupled to structure 22. Typically, the number of sutures 130 coupled to structure 22 is determined in accordance with the size of the dilated annulus, and thereby the number of anchoring sites needed in order to properly anchor structure 22 to the dilated annulus.

Figure 11:
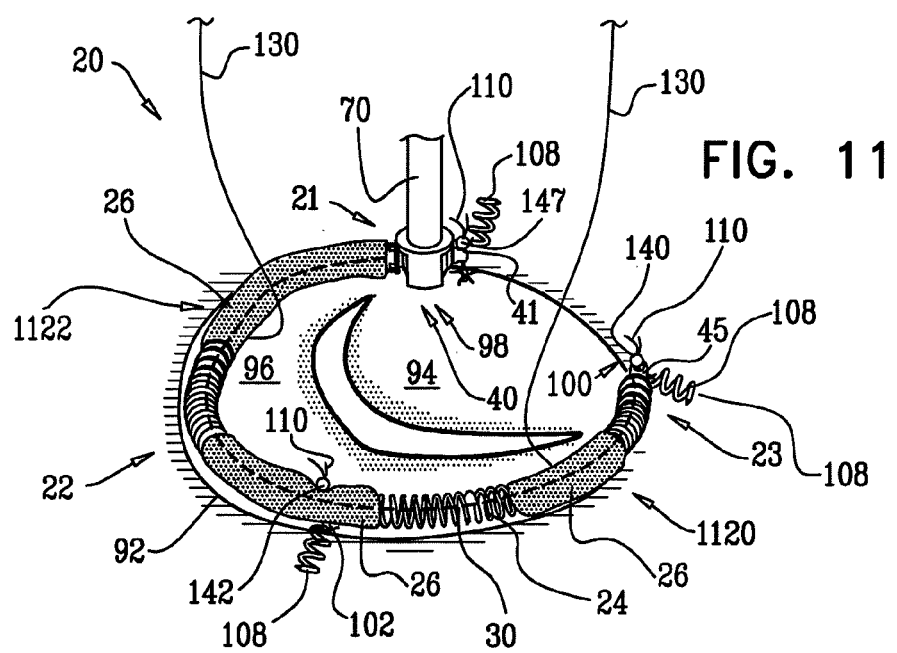

FIG. 11 shows structure 22 following the positioning and initial suturing thereof to annulus 92. Respective beads 140, 142, and 147 are slid along sutures 110 toward an upper surface of structure 22. Beads 140, 142, and 147 each comprise a crimping mechanism which crimps sutures 110 and, thereby beads 140, 142, and 147 lock sutures 110 in place with respect to structure 22, thereby locking in place structure 22 with respect to annulus 92. Excess portions of sutures 110 are clipped proximally to beads 140, 142, and 147 and removed from within the heart of the subject.

Following the initial locking of structure 22 with respect to annulus 92, sutures 130 remain extending from structure 22 and accessible from outside the body of the subject. Sutures 130 facilitate advancement of anchors toward structure 22 in order to further anchor structure 22 to annulus 92 at locations 1120 and 1122. It is to be noted that two sutures 130 are shown by way of illustration and not limitation, and that any suitable number of sutures 130 may be coupled to structure 22.

Following implantation of structure 22 along annulus 92 and prior to contraction of structure 22, structure 22 provides a partial annuloplasty ring, or band, having a distance between first and second ends 21 and 23 of structure 22 such that structure 22 defines a first perimeter thereof.

FIGS. 12A-B show further anchoring of structure 22 to annulus 92. A sheath 151 has a lumen which houses an anchor advancement tube 150, which in turn, has a lumen thereof. Sheath 151 and advancement tube 150 are advanced along suture 130 and toward structure 22. A distal end of anchor advancement tube 150 is coupled to an anchor which is used to anchor structure 22 to annulus 92. Typically, the anchor is advanced to annulus 92 with respect to structure 22. In some embodiments, the anchor is advanced through body portion 24, as shown in FIGS. 12A-B. In some embodiments, the anchors are advanced through braided mesh 26 that surrounds body portion 24.

FIG. 12A shows the anchor comprising a helical anchor 108 having a pointed distal tip. Anchor 108 is corkscrewed with respect to the compressible element of body portion 24 such that helical anchor 108 intertwines with the compressible element of body portion 24 and is thereby coupled to the compressible element. Further corkscrewing of helical anchor 108 advanced a distal portion of anchor 108 beyond structure 22 and into tissue of annulus 92, thereby further anchoring structure 22 to annulus 92.

FIG. 12B shows the anchor comprising a pronged anchor 105 having a substantially rigid, body portion and a plurality of prongs 107 each having a pointed distal end. Body portion of anchor 105 is coupled to structure 22 and prongs 107 are advanced through tissue of annulus 92. Typically, anchor 105 comprises a shape-memory alloy, e.g., nitinol, which enables prongs 107 to transition from the substantially straight configuration, to a curved configuration in which each prong 107 curves proximally to assume a substantially "U"-shaped configuration, as shown. Typically, during advancement of anchor 105 toward structure 22, anchor 105 is disposed within sheath 151 in a configuration in which prongs are aligned in a straight configuration.

It is to be noted that anchor 105 is shown as comprising two prongs 107 by way of illustration and not limitation, and that any suitable number or prongs may be used.

Typically, anchor 105 is compressed within a tubular housing prior to being advanced through tissue of the annulus. The tubular housing is first advanced through the annuloplasty structure prior to the pushing of anchor 105 from within the tubular housing and into tissue of the annulus. In some embodiments, the tubular housing comprises anchor advancement tube 150 which is first advanced through a portion of the annuloplasty structure, e.g., is advanced between adjacent coils of the annuloplasty structure, prior to advancing anchor 105 from within tube 150 and into tissue of the annulus. As anchor 105 penetrates tissue of annulus 92, prongs 107 gradually bend away from a longitudinal axis of the body portion of anchor 105 in order to assume their respective bent configurations. As prongs 107 assume their respective bent configurations, their pointed ends puncture surrounding tissue in order to further anchor 105 to tissue of the patient. In its expanded, bent configuration, anchor 105 is configured to restrict proximal motion of thereof through the tissue.

Once structure 22 is further anchored to annulus 92, a respective bead 146 and 148 is advanced along each suture 130 and toward an upper surface of structure 22 (FIG. 13). Beads 146 and 148 lock in place structure 22 at locations 1120 and 1122, respectively, in a manner as described hereinabove with respect to beads 140, 142, and 147. Following the advancing of beads 146 and 148 toward the upper surface of structure 22, excess portions of sutures 130 are clipped proximally to beads 146 and 148 and are removed from the heart of the subject.

FIG. 13 shows the contracting annulus 92 in response to the contracting of structure 22. Structure is typically contracted only following the locking in place structure 22 to annulus 92 by the beads. The flexible rod housed within tool 70 (as described hereinabove with reference to FIGS. 4-7, and 8A-B) is pushed downward, as shown by arrow 1, in order to release locking mechanism 145 from spool 46 of contracting mechanism 40, as described hereinabove. Once free of locking mechanism 145, spool 46 is rotated in response to a rotational force applied thereto by tool 70, as indicated by arrow 2. Rotation of spool 46 contracts structure 22, by wrapping at least a portion of member 30 around spool 46, and thereby pulling on the second end of flexible member 30 toward the first end of flexible member 30 such that flexible member pulls on second end 23 of structure 22 toward first end 21 of structure 22 (in a direction as indicated by arrow 3), as described hereinabove with reference to FIGS. 2 and 3. At the same time, first end 21 of structure 22 is pulled toward second end 23 of structure 22.

Following the contraction of structure 22, first and second ends 21 and 23, respectively, of structure 22 are pulled toward each such that structure assumes a second perimeter. The second perimeter following the contracting of structure 22 is smaller than the first perimeter of structure 22 prior to the contracting. Structure 22 may be contracted such that the second perimeter defines any suitable dimension.

It is to be noted that structure 22 may be anchored to annulus 92 such that structure 22 is positioned along the entire perimeter of annulus 92. Alternatively, structure 22 may be anchored to annulus 92 such that it is positioned partially along the perimeter of annulus 92.

Figure 14A:
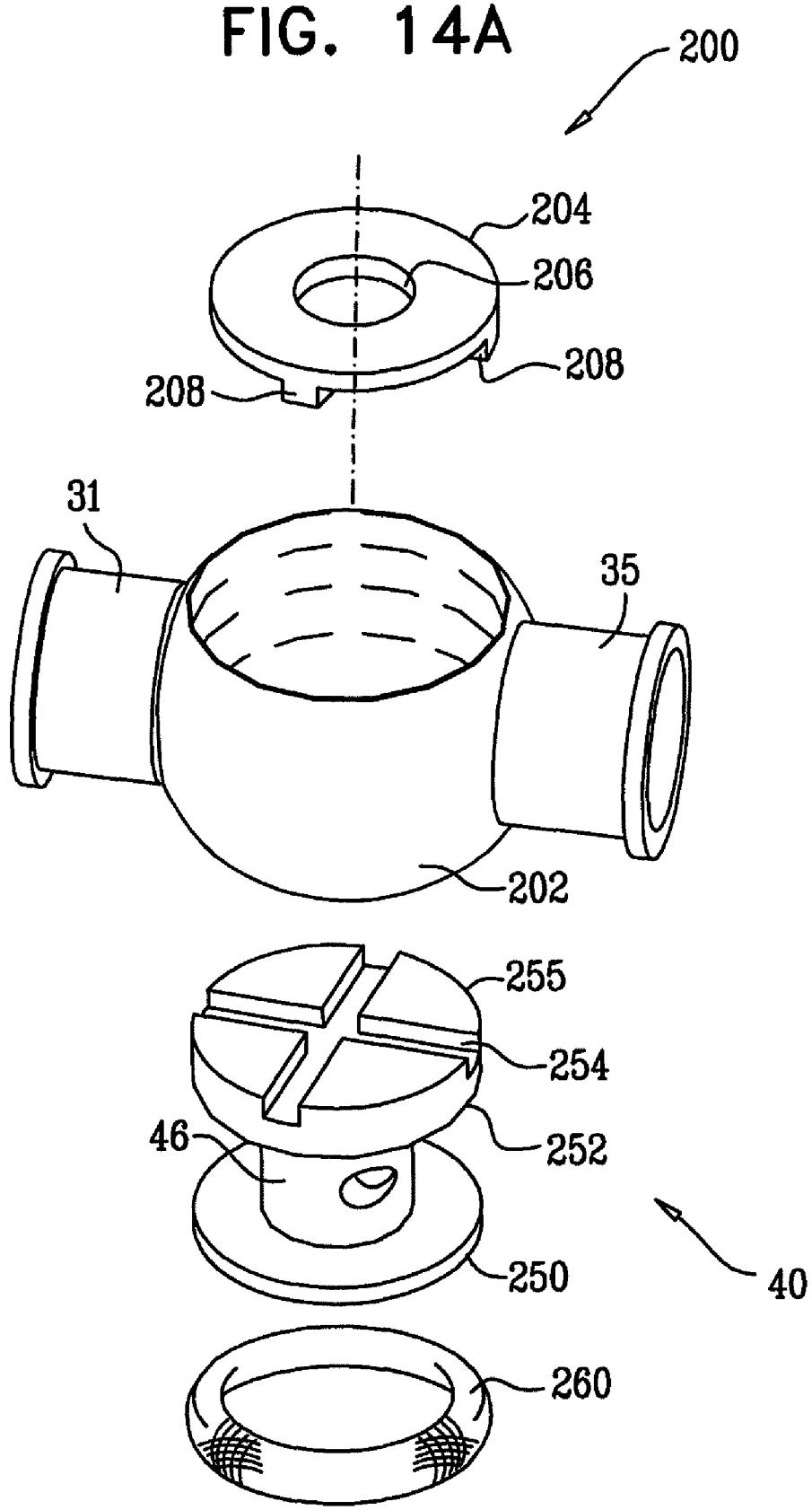
FIGS. 14A-C are schematic illustrations of a locking mechanism used to lock the contracting mechanism, in accordance with an embodiment of the present invention.
Figure 14B:
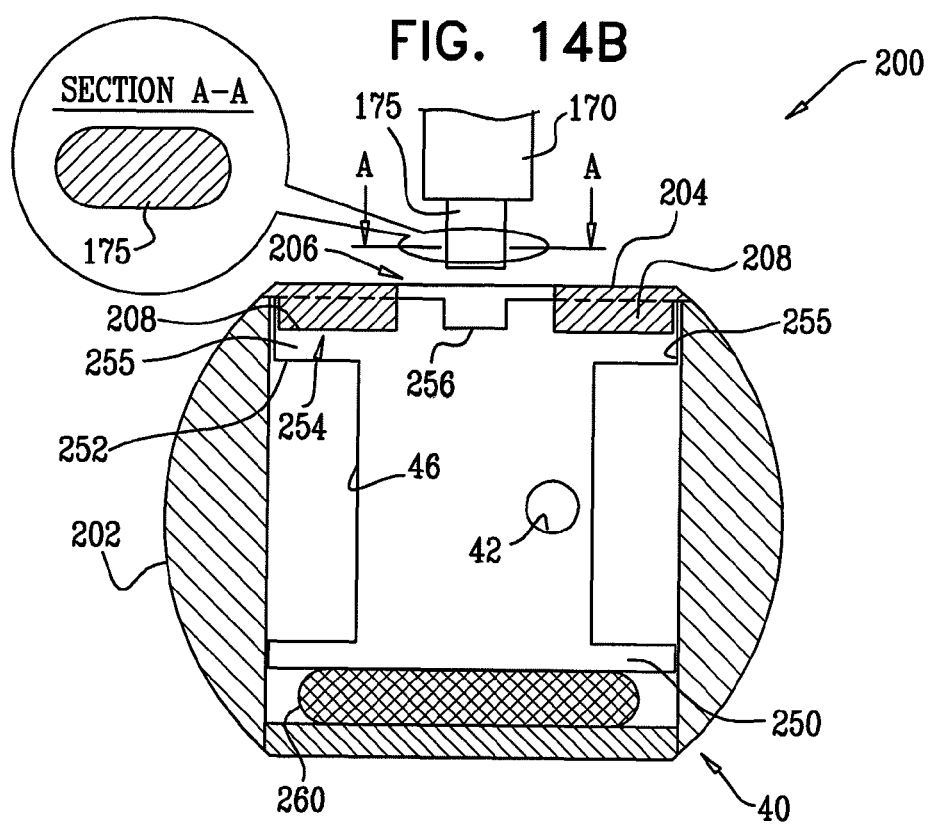
Figure 14C:
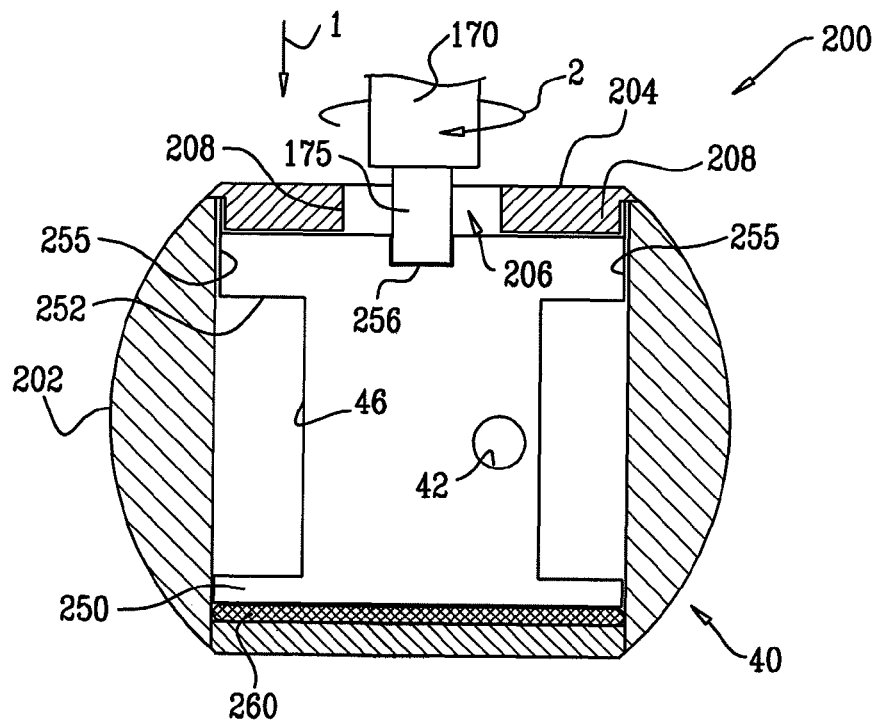

Reference is now made to FIGS. 14A-C, which are schematic illustrations of a locking mechanism 200 configured to lock in place contracting mechanism 40 of the annuloplasty structures described herein, in accordance with an embodiment of the present invention. Locking mechanism 200 is disposed within housing 202, that is similar to housings 44 and 144 described hereinabove, with the exception that an underside of a planar upper surface 204 of housing 202 is shaped to define a plurality of projections 208 which (a) project out of a plane defined by planar upper surface 204 and downward into the body of housing 202, and (b) engage spool 46.

FIG. 14A shows components of locking mechanism 200. Upper surface 204 is welded or soldered to the body of housing 202. Spool 46, in turn has an upper portion 252 and a lower portion 250. Upper portion 252 is shaped to provide raised surfaces 255 which define a plurality of recesses 254. Although four recesses 254 are shown by way of illustration and not limitation, it is to be noted that any suitable number of recesses 254 may be provided, e.g., between 1 and 10 recesses. In turn, upper surface 204 may be shaped to provide a suitable number of projections 208, e.g., between 1 and 10 projections. Lower portion 250 of spool 46 rests against a compressible element 260, e.g., a spring or stent-like element (as shown), that is coupled to a lower portion of housing 202.

Recesses 254 of upper portion 252 of spool are is shaped to define a screw-driver-engaging recess 256 extending 0.1-2.0 mm downward from an upper surface of spool 46. Recess 256 provides a means by which an elongate tool engages and facilitates rotation spool 46. Typically, a distal portion of the elongate tool is advanced through an opening 206 in upper surface 204 of housing 202 prior to engaging spool 46 via recess 256. As shown hereinbelow, opening 206 is shaped to accommodate a size of a screwdriver tool.

Typically, recesses 254 are disposed along a circumference of at least a portion of upper portion 252 of spool 46. Similarly, projections 208 of upper surface 204 of housing 202 are disposed along a circumference of at least a portion of upper surface 204 of housing 202.

FIG. 14B shows locking mechanism 200 in a resting state thereof. Lower portion 250 of spool 46 rests against compressible element 260 in a relaxed, uncompressed state thereof. As such, in the resting state of locking mechanism 200, upper portion 252 of spool 46 contacts upper surface 204 of housing 202 in a manner in which projections 208 of upper surface 204 are disposed within recesses 254 of upper surface 252 of spool 46. In such a manner, by being disposed within respective recesses 254 of spool 46, projections 208 restrict rotation spool 46.

FIG. 14C shows the unlocking of locking mechanism 200 in response to the disengaging of spool 46 from upper surface 204 of housing 202. A distal portion of an elongate tool 170 is advanced through hole 206 defined by upper surface 204, and subsequently into recess 256 provided by upper portion 252 of spool 46. Tool 170 is shaped to define a distal screwdriver portion 175 that first within recess 256 of spool 46 that is defined by grooves 154. As shown in FIG. 14B, screwdriver portion 175 is shaped to define an elliptical cross-section by way of illustration and not limitation. For example, screwdriver portion 175 is shaped to define a rectangular cross-section. In some embodiments, screwdriver portion 175 is shaped to define a "T"-shaped cross-section.

Tool 170 is pushed downward, as indicated by arrow 1, thereby pushing downward spool 46 and, responsively, compressing compressible element 260. In response to the compressing of compressible element 260, upper portion 252 of spool 46 is distanced from upper surface 204 of housing 202, and thereby, projections 208 are dislodged from within recesses 264 of upper portion 252 of spool 46. Once locking mechanism 200 is unlocked and spool 46 is free of projections 208, tool 170 is rotated (in the direction as indicated by arrow 2) in order to rotate spool 46 and wrap flexible member 30 therearound, thereby facilitating contracting of the annuloplasty structure responsively to the rotating.

Following the rotating of spool 46 and the responsive contracting of the annuloplasty structure, tool 170 is pulled away from spool 46, allowing compressible element 260 to assume its relaxed, uncompressed state. As compressible element 260 assumes its relaxes, uncompressed state, compressible element 260 pushed spool 46 upwards in a manner in which recesses 254 are once again engaged by projections 208 of upper surface 204 of housing 202. Such engaging locks spool 46 in place and restricts rotation thereof.

It is to be noted that tool 170 may also be used to expand the annuloplasty structure by rotating in a direction that is opposite the direction used in order to contract the annuloplasty structure.

Figure 15:
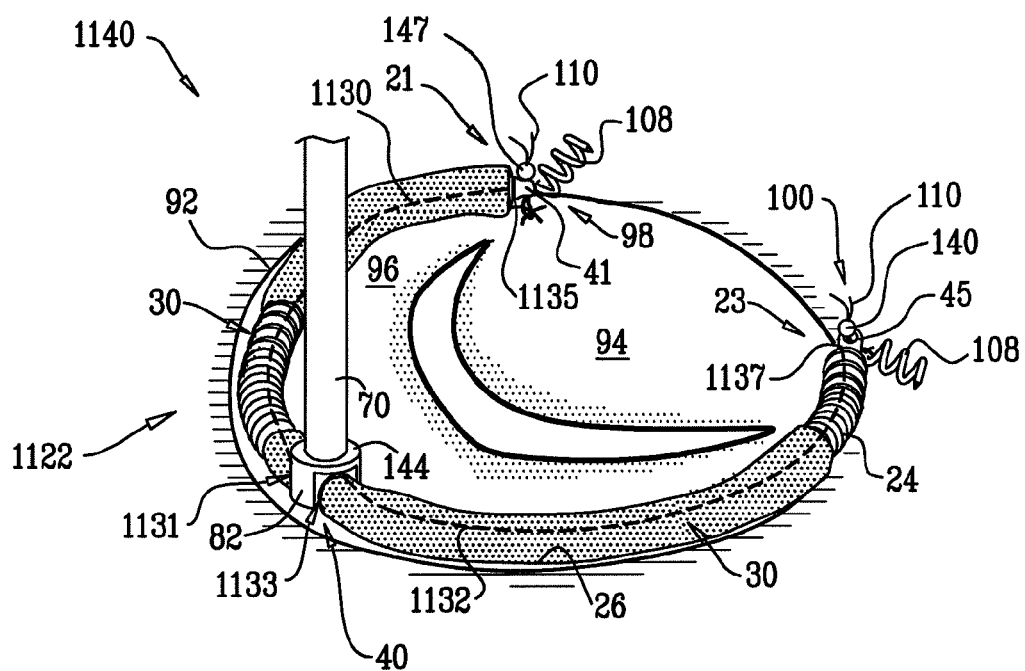
FIG. 15 is a schematic illustration of an annuloplasty structure for contracting the annulus, in accordance with another embodiment of the present invention.

FIG. 15 shows a system 1140 comprising an annuloplasty structure 1122 comprising contracting mechanism 40 coupled to two flexible members 30, in accordance with an embodiment of the present invention. Structure 1122 comprises a body portion 24 having a compressible element, as described hereinabove. Body portion 24 is typically surrounded by braided mesh 26, as described hereinabove.

It is to be noted that portions of braided mesh 26 are shown for clarity of illustration and that body portion 24 of structure 1122 may be entirely surrounded by braided mesh 26. Contracting mechanism 40 is disposed with respect to structure 1122 at a portion thereof that is between first and second ends 21 and 23 thereof, e.g., at the center, as shown by way of illustration and not limitation.

Contracting mechanism 40 comprises a spool 46 as described hereinabove. Spool 46 of contracting mechanism 40 of system 1140 is coupled to a first end 1131 of a first flexible member 1130 and to a first end 1133 of a second flexible member 1132. A second end 1135 of first flexible member 1130 is coupled to first end 21 of structure 1122. A second end 1137 of second flexible member 1132 is coupled to second end 23 of structure 1122. Flexible members 1130 and 1132 each comprise a wire, a ribbon, a rope, or a band, comprising a flexible metal.

During rotation of spool 46 of contracting mechanism 40, as described hereinabove, respective portions of first and second flexible members 1130 and 1132 are wrapped around spool 46. Responsively to the winding of the portions of first and second flexible members 1130 and 1132 around spool 46, second ends 1135 and 1137 of flexible members 1130 and 1132, respectively, are pulled toward contracting mechanism 40. As second ends 1135 and 1137 of flexible members 1130 and 1132, respectively, are pulled toward contracting mechanism 40, first and second ends 21 and 23 of structure 1122 are pulled toward contracting mechanism 40, thereby drawing together first and second ends 21 and 23.

Reference is made to FIGS. 9-11, 12A-B, 13, 14A-C, and 15. It is to be noted that although structure 22 is shown as being implanted along annulus 92, structure 122 (as described hereinabove with reference to FIGS. 5, 6A-B, 7, and 8A-B) and structure 1122 (as described hereinabove with reference to FIG. 15) may be implanted along annulus 92 in a similar manner. Since structure 122 does not comprise suture fasteners 41 and 45, sutures are threaded through braided sheath 26 of structure 122 at respective locations along the "D"-shaped ring. As described hereinabove, structure 122 is placed along annulus 92 such that portions 49 of structure 122 are disposed between the trigones of the heart.

For embodiments in which structure 122 is transcatheterally advanced toward annulus 92, structure 122 may be folded, or otherwise collapsed, such that it fits within the lumen of the advancement catheter.

Reference is again made to FIGS. 9-11, 12A-B, 13, 14A-C, and 15. It is to be noted that for embodiments in which structures 22 and 122 are implanted during an open-heart or minimally-invasive procedure, an incision is made in the heart, and a plurality of sutures are sutured along the annulus are used to facilitate advancement of the annuloplasty structure toward the annulus. Prior to advancement of the annuloplasty structure, portions of the plurality of sutures are threaded through respective portions of the annuloplasty structure. A tool which delivers and facilitates contraction of the annuloplasty structure is coupled to the annuloplasty structure and advances the annuloplasty structure toward the annulus. Once the annuloplasty structure is positioned along the annulus and anchored thereto, the incision is closed around the tool using a purse string stitch. The subject is removed from the cardiopulmonary bypass pump and the heart is allowed to resume its normal function. While the heart is beating, the annuloplasty structure is then contracted, as described hereinabove, and responsively, the annulus is contracted.

Reference is yet again made to FIGS. 9-11, 12A-B, 13, 14A-C, and 15. It is to be noted that the annuloplasty structure may be advanced toward the annulus using any suitable delivery tool. Following the positioning of the annuloplasty structure along the annulus, the delivery tool is disengaged from the annuloplasty structure. Then, tool 70 may be advanced toward housing 44 and engage spool 46. In some embodiments, tool 70 is advanced toward the annuloplasty structure along a suture coupled to the annuloplasty structure at one end and accessible outside the body of the subject and another end.

It is to be noted that for embodiments in which structures 22 122, and 1122 are implanted during an open-heart or minimally-invasive procedure, structures 22, 122, and 1122 may be provided independently or in combination with sutures 130.

Reference is now made to FIGS. 1-15. It is to be noted that the contraction of structures 22, 122, and 1122 described herein is reversible. That is, rotating spool 46 in a rotational direction that opposes the rotational direction used to contract the annuloplasty structure, unwinds a portion of flexible member 30 from around spool 46. Unwinding the portion of flexible member 30 from around spool 46 thus feeds the portion of flexible member 30 back into the lumen of body portion 24 of structures 22, 122, and 122, thereby slackening the remaining portion of flexible member 30 that is disposed within the lumen of body portion 24. Responsively, the annuloplasty structure gradually relaxes (i.e., with respect to its contracted state prior to the unwinding) as the compressible element of body portion 24 gradually expands.

Reference is again made to FIGS. 1-15. It is to be noted that structures 22, 122, and 1122 may be stapled to the annulus using techniques known in the art.

Reference is yet again made to FIGS. 1-15. It is to be noted that following initial contraction of annuloplasty structures 22, 122, and 1122, structures 22, 122, and 1122 may be further contracted or relaxed at a later state following the initial implantation thereof. Using real-time monitoring, tactile feedback and optionally in combination with fluoroscopic imaging, tools 70 and 170 used to contract or relax annuloplasty structures 22, 122, and 1122 may be reintroduced within the heart and engage spools 46.

Reference is yet again made to FIGS. 1-15. It is to be noted that flexible member 30 may be disposed outside the lumen defined by structures 22, 122, and 1122. For example, flexible member 30 may be disposed alongside an outer wall of structures 22, 122, and 1122. In such an embodiment, structures 22, 122, and 1122 may not be shaped to define tubular structures having respective lumens thereof, but rather be shaped as bands or ribbons which are not shaped to define a lumen.

It is to be noted that systems 20, 120, and 1140 for repairing a dilated annulus of the subject may be used to treat a valve of the subject, e.g., the tricuspid valve. It is to be still further noted that systems described herein for treatment of valves may be used to treat other annular muscles within the body of the patient. For example, the systems described herein may be used in order to treat a sphincter muscle within a stomach of the subject.

For some applications, techniques described herein are practiced in combination with techniques described in one or more of the references cited in the Background section and Cross-references section of the present patent application.

Additionally, the scope of the present invention includes embodiments described in one or more of the following:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed on Dec. 5, 2007;

U.S. Provisional Patent Application 61/132,295 to Gross et al., entitled, "Annuloplasty devices and methods of delivery therefor," filed on Jun. 16, 2008;

U.S. Pat. No. 7,431,692 to Zollinger et al.; and

U.S. Patent Application Publication 2007/0016287 to Cartledge et al.

All of these applications are incorporated herein by reference. Techniques described herein can be practiced in combination with techniques described in one or more of these applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. Apparatus comprising an annuloplasty ring structure configured to be implanted in a body of a subject, comprising:
    an implant structure with a coiled structure having a lumen and first and second portions, the implant structure comprising a rotatable structure coupled to the implant structure in a vicinity of the first portion thereof;

and a flexible member that does not form a closed loop disposed within the lumen of the coiled structure, the flexible member having a first portion thereof that contacts the rotatable structure, and at least one end thereof that does not contact the rotatable structure, wherein:

in response to rotation of the rotatable structure in a first rotational direction, successive portions of the first portion of the flexible member advance in a first advancement direction toward and wind around a portion of the apparatus, so that and the flexible member contracts the implant structure and, wherein the apparatus is implanted at a cardiac valve of the subject.

2. The apparatus according to claim 1, wherein the successive portions of the first portion of the flexible member are configured to be advanced in a second advancement direction with respect to the rotatable structure and thereby to facilitate expansion of the implant structure in response to rotation of the rotatable structure in a second rotational direction, the second rotational direction being opposite the first rotational direction, and the second advancement direction being opposite the first advancement direction.

3. The apparatus according to claim 1, wherein the implant structure comprises expanded polytetrafluoroethylene (ePTFE).

4. The apparatus according to claim 1, wherein the implant structure is coated with polytetrafluoroethylene.

5. The apparatus according to claim 1, wherein:
the implant structure is configured to be implanted along an annulus of a mitral valve of the subject, and
the implant structure is configured to contract the annulus in response to the contraction of the implant structure.

6. The apparatus according to claim 1, wherein the annuloplasty ring structure comprises a full annuloplasty ring, and wherein the second portion of the implant structure is coupled to the rotatable structure in a manner that causes the implant structure to be shaped to define the full annuloplasty ring.

7. The apparatus according to claim 1, wherein the apparatus is configured to be implanted along an annulus of a mitral valve of the subject, and wherein the apparatus is configured to be transcatheterally advanced toward the annulus.

8. The apparatus according to claim 1, further comprising a locking mechanism coupled to the implant structure and configured to restrict rotation of the rotatable structure.

9. The apparatus according to claim 1, wherein:
the first and second portions of the implant structure are disposed adjacently to first and second ends of the implant structure, respectively,
the apparatus is configured to be implanted along an annulus of a mitral valve of the subject in a manner in which the first end of the implant structure is distanced from the second end of the implant structure, and
the implant structure in its implanted state defines a partial annuloplasty ring.

10. The apparatus according to claim 1, wherein:
the apparatus is configured to be implanted along an annulus of a mitral valve of the subject,
the first portion of the implant structure is configured to be coupled to a first location along the annulus in a vicinity of a first trigone adjacent to the mitral valve, and
the second portion of the implant structure is configured to be coupled to a second location along the annulus in a vicinity of a second trigone adjacent to the mitral valve.

11. The apparatus according to claim 10, wherein:
the implant structure is shaped to provide first and second ends in communication with the first and second portions, respectively,
the first end is configured to be coupled to the first location along the annulus in the vicinity of the first trigone adjacent to the mitral valve, and
the second end of the implant structure is configured to be coupled to the second location along the annulus in the vicinity of the second trigone adjacent to the mitral valve.

12. The apparatus according to claim 1, wherein:
the first portion of the implant structure has first and second ends, the first end of the first portion being coupled to the rotatable structure,
the second portion of the implant structure has first and second ends, the first end of the second portion being coupled to the rotatable structure,
the flexible member defines a first flexible member and the apparatus further comprises a second flexible member, each of the first and second flexible members having respective first and second ends,
the first end of the first flexible member is coupled to the rotatable structure, and the second end of the first flexible member is coupled to the implant structure in a vicinity of the second end of the first portion, and
the first end of the second flexible member is coupled to the rotatable structure, and the second end of the second flexible member is coupled to the implant structure in a vicinity of the second end of the second portion.

13. The apparatus according to claim 12, wherein in response to rotation of the rotatable structure in the first rotational direction, successive portions of the respective first and second flexible members advance in respective first advancement directions with respect to the rotatable structure and contact the rotatable structure, and, responsively, pull the respective second ends of the first and second flexible members toward the rotatable structure, and responsively draw the first and second portions of the implant structure toward each other.

14. The apparatus according to claim 1, wherein:
the apparatus is configured to be implanted along an annulus of a mitral valve of a heart of the subject,
a first section of the implant structure is flexible and longitudinally compressible, and
a second section of the implant structure is in series with the first section of the implant structure, the second section being flexible and less longitudinally compressible than the first section.

15. The apparatus according to claim 14, wherein the second section is not longitudinally compressible.

16. The apparatus according to claim 14, wherein a radius of curvature at a center of the first section is smaller than a radius of curvature at a center of the second section, when no external force is applied to the implant structure.

17. The apparatus according to claim 14, wherein the second section of the implant structure has first and second ends thereof and a body portion disposed between the first and second ends, the second section of the implant structure being configured to be disposed along a portion of the annulus in a manner in which:
the first end of the second section is configured to be coupled to the annulus in a vicinity of a left trigone of the heart that is adjacent to the mitral valve of the subject,
the second end of the second section is configured to be coupled to the annulus in a vicinity of a right trigone of the heart that is adjacent to the mitral valve, and the body portion is configured to be disposed along the annulus in a vicinity of the annulus that is between the left and right trigones.

18. The apparatus according to claim 17, wherein the body portion disposed between the first and second ends of the second section of the implant structure has a length of 10-50 mm.

19. The apparatus according to claim 1, wherein the apparatus is configured to be implanted along an annulus of a mitral valve of the subject in a manner in which the implant structure is formed into at least a portion of an annuloplasty ring.

20. The apparatus according to claim 19, further comprising a plurality of sutures, each suture of the plurality of sutures being configured to be fastened to a respective location along a circumference of the annulus of the subject, the plurality of sutures being configured to facilitate advancement of the implant structure toward the annulus.

21. The apparatus according to claim 20, wherein the plurality of sutures are configured to be coupled to the implant structure at respective locations thereof that are in parallel with the respective locations along the circumference of the annulus of the subject, and wherein the implant structure is formed into the at least the portion of the annuloplasty ring in response to the coupling.

22. The apparatus according to claim 1, wherein the implant structure is compressible along a longitudinal axis of the implant structure.

23. The apparatus according to claim 22, wherein, in response to rotation of the rotatable structure, the flexible member is configured to longitudinally compress the implant structure.

24. The apparatus according to claim 1, further comprising a plurality of sutures configured to be coupled to an annulus of a mitral valve of the subject and to facilitate implantation of the implant structure along the annulus.

25. The apparatus according to claim 24, further comprising a plurality of anchors respectively coupled to the plurality of sutures and configured to be anchored to tissue of the annulus of the subject.

26. The apparatus according to claim 25, wherein the plurality of anchors are configured to lock the implant structure in place with respect to the annulus.

27. The apparatus according to claim 25, wherein the plurality of anchors are configured to be implanted along a circumference of the annulus, and to be coupled to the implant structure in a manner which forms the implant structure into a curved configuration.

28. The apparatus according to claim 1, wherein:
the rotatable structure has a first end shaped to define a first opening, and a second end shaped to define a second opening, the rotatable structure being shaped to define a channel extending from the first opening to the second opening, the channel being configured for passage therethrough of an elongate tool, and
the second end of the rotatable structure has a lower surface thereof shaped to:
define one or more recesses.

29. The apparatus according to claim 28, further comprising a mechanical element having a planar surface coupled to the lower surface of the rotatable structure, the mechanical element being shaped to provide:
a protrusion protruding out of a plane of the planar surface of the mechanical element, the protrusion being disposed within one of the recesses during a resting state of the mechanical element, in a manner that restricts rotation of the rotatable structure, and
a depressible portion coupled to the protrusion, the depressible portion being disposed in communication with the second opening of the second end of the rotatable structure, and configured to dislodge the protrusion from within the recess in response to a force applied thereto by the elongate tool.

30. The apparatus according to claim 1, wherein:
the rotatable structure has a first end and a second end, the first end being shaped to receive a portion of a tool, and
the first end of the rotatable structure has an upper surface thereof shaped to:
define one or more recesses.

31. The apparatus according to claim 30, further comprising:
a mechanical element having a planar surface coupled to the upper surface of the rotatable structure, the mechanical element being shaped to provide at least one protrusion protruding out of a plane of the planar surface of the mechanical element, the protrusion being disposed within one of the recesses during a resting state of the mechanical element, in a manner that restricts rotation of the rotatable structure; and
a compressible element coupled to the second end of the rotatable structure, the compressible element being configured to be compressed and facilitate dislodging of the protrusion from within the recess in response to a force applied to the rotatable structure by the elongate tool.

32. The apparatus according to claim 1, wherein the rotatable structure comprises a spool, and wherein, in response to the rotation of the spool in the first rotational direction, the successive portions of the first portion of the flexible member are configured to be wound around the spool.

33. The apparatus according to claim 1, wherein the flexible member comprises a body portion that is between the first portion and the at least one end, and wherein the body portion applies a pulling force, in the first advancement direction, to the at least one end in response to the advancement of the successive portions of the first portion of the flexible member.

34. The apparatus according to claim 1, wherein in response to rotation of the rotatable structure in the first rotational direction, the successive portions of the first portion of the flexible member advance only in the first advancement direction with respect to the rotatable structure.

* * * * *

UNITED STATES PATENT AND TRADEMARK OFFICE
CERTIFICATE OF CORRECTION

PATENT NO.        : 8,241,351 B2
APPLICATION NO.   : 12/341960
DATED             : August 14, 2012
INVENTOR(S)       : Oz Cabiri Page 1 of 1

It is certified that error appears in the above-identified patent and that said Letters Patent is hereby corrected as shown below:

In the Specification:

Column 20, line 28, please insert --anchor-- after anchor. The word should appear twice.

In the Claims:

Column 25, line 10, please delete "and".

Signed and Sealed this
Fifth Day of August, 2014

Michelle K. Lee
*Deputy Director of the United States Patent and Trademark Office*